(12) United States Patent
Takemoto

(10) Patent No.: US 7,611,822 B2
(45) Date of Patent: Nov. 3, 2009

(54) SALT SUITABLE FOR AN ACID GENERATOR AND A CHEMICALLY AMPLIFIED POSITIVE RESIST COMPOSITION CONTAINING THE SAME

(75) Inventor: Ichiki Takemoto, Kawanishi (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/219,453

(22) Filed: Jul. 22, 2008

(65) Prior Publication Data

US 2009/0042128 A1 Feb. 12, 2009

(30) Foreign Application Priority Data

Jul. 25, 2007 (JP) .............................. 2007-193184

(51) Int. Cl.
*G03F 7/004* (2006.01)
*C07C 69/74* (2006.01)

(52) U.S. Cl. .................... 430/270.1; 430/905; 430/907; 430/910; 430/921; 430/922; 560/126; 562/109; 562/113

(58) Field of Classification Search .............. 430/270.1, 430/905, 910, 921, 922; 560/126; 562/109, 562/113
See application file for complete search history.

(56) References Cited

U.S. PATENT DOCUMENTS

| | | | |
|---|---|---|---|
| 7,262,321 B2 * | 8/2007 | Harada et al. ............... | 560/129 |
| 7,301,047 B2 * | 11/2007 | Yoshida et al. .............. | 560/129 |
| 7,371,505 B2 * | 5/2008 | Kodama .................. | 430/270.1 |
| 2006/0194982 A1 * | 8/2006 | Harada et al. ............... | 560/150 |
| 2007/0027336 A1 * | 2/2007 | Yoshida et al. .............. | 560/129 |
| 2007/0184382 A1 * | 8/2007 | Yamaguchi et al. ......... | 430/270.1 |

FOREIGN PATENT DOCUMENTS

| | | |
|---|---|---|
| GB | 2 447 789 A | 9/2008 |
| JP | 11-52575 | 2/1999 |
| JP | 2004-4561 | 1/2004 |
| WO | WO-2006/133330 A1 | 12/2006 |
| WO | WO-2008/099869 A1 | 8/2008 |

OTHER PUBLICATIONS

CAS Abstract Acc. No. 2008:1008950, Hagiwara et al. WO 2008/099869 published Aug. 21, 2008.

* cited by examiner

*Primary Examiner*—John S Chu
(74) *Attorney, Agent, or Firm*—Birch, Stewart, Kolasch & Birch, LLP

(57) ABSTRACT

The present invention provides a salt represented by the formula (I):

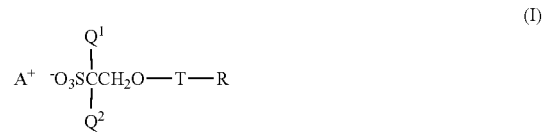

wherein $Q^1$ and $Q^2$ each independently represent a fluorine atom or a C1-C6 perfluoroalkyl group, T represents a methylene group or a carbonyl group, R represents an adamantyl group substituted with at least one selected from the group consisting of a C1-C4 alkyl group, a C1-C4 alkoxy group, a hydroxyl group, a hydroxymethyl group, a cyano group and an oxo group, and $A^+$ represents an organic counter ion.

The present invention further provides a chemically amplified resist composition comprising the salt represented by the above-mentioned formula (I).

17 Claims, No Drawings

SALT SUITABLE FOR AN ACID GENERATOR AND A CHEMICALLY AMPLIFIED POSITIVE RESIST COMPOSITION CONTAINING THE SAME

This nonprovisional application claims priority under 35 U.S.C. § 119(a) on Patent Application No. 2007-193184 filed in JAPAN on Jul. 25, 2007, the entire contents of which are hereby incorporated by reference.

FIELD OF THE INVENTION

The present invention relates to a salt suitable for an acid generator used for a chemically amplified resist composition which is used in fine processing of semiconductors, and a chemically amplified positive resist composition containing the same.

BACKGROUND OF THE INVENTION

A chemically amplified positive resist composition used for semiconductor microfabrication employing a lithography process contains an acid generator comprising a compound generating an acid by irradiation.

In semiconductor microfabrication, it is desirable to form patterns having an excellent pattern shape, and it is expected for a chemically amplified resist composition to give such patterns.

JP 2004-4561A discloses a chemically amplified resist composition containing the salt represented by the following formula:

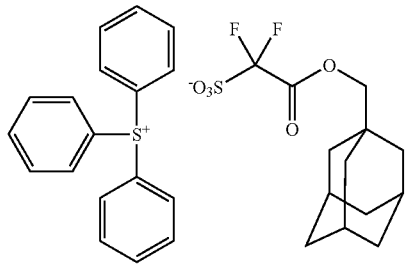

as the acid generator.

SUMMARY OF THE INVENTION

The present invention is provided a salt suitable for an acid generator capable of providing chemically amplified resist compositions giving patterns having an excellent pattern shape, and a chemically amplified resist composition containing the salt.

The present invention relates to the followings:

<1> A salt represented by the formula (I):

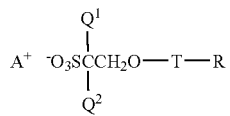

wherein $Q^1$ and $Q^2$ each independently represent a fluorine atom or a C1-C6 perfluoroalkyl group, T represents a methylene group or a carbonyl group, R represents an adamantyl group substituted with at least one selected from the group consisting of a C1-C4 alkyl group, a C1-C4 alkoxy group, a hydroxyl group, a hydroxymethyl group, a cyano group and an oxo group, and $A^+$ represents an organic counter ion;

<2> The salt according to <1>, wherein $Q^1$ and $Q^2$ each independently represent a fluorine atom or a trifluoromethyl group;

<3> The salt according to <1>, wherein $Q^1$ and $Q^2$ represent fluorine atoms;

<4> The salt according to <1>, <2> or <3>, wherein the organic counter ion is at least one cation selected from the group consisting of a cation represented by the formula (IIa):

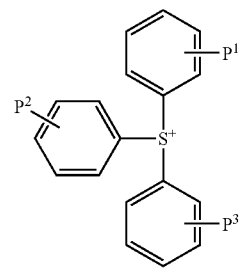

wherein $P^1$, $P^2$ and $P^3$ each independently represent a hydrogen atom, a hydroxyl group, a C1-C12 alkyl group or a C1-C12 alkoxy group, a cation represented by the formula (IIb):

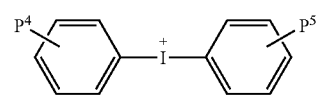

wherein $P^4$ and $P^5$ each independently represent a hydrogen atom, a hydroxyl group, a C1-C12 alkyl group or a C1-C12 alkoxy group, a cation represented by the formula (IIc):

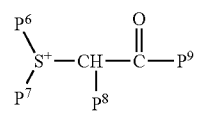

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (IId):

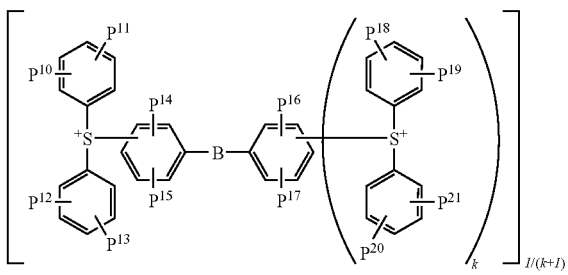
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1;

<5> The salt according to <1>, <2> or <3>, wherein the organic counter ion is a cation represented by the formula (IIa);

<6> The salt according to <5>, wherein the cation represented by the formula (IIa) is a cation represented by the formula (IIe):

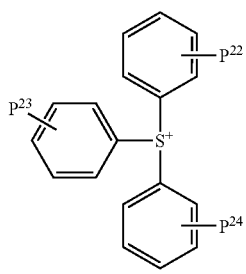
(IIe)

wherein $P^{22}$, $P^{23}$ and $P^{24}$ each independently represent a hydrogen atom or C1-C4 alkyl group;

<7> The salt according to any one of <1> to <6>, wherein R represents an adamantyl group substituted with a hydroxyl group or an oxo group.

<8> The salt according to any one of <7>, wherein the organic counter ion is a cation represented by the formula (IIe):

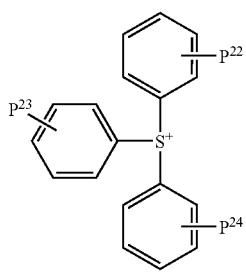
(IIe)

wherein $P^{22}$, $P^{23}$ and $P^{24}$ each independently represent a hydrogen atom or C1-C4 alkyl group;

<9> A chemically amplified positive resist composition comprising a salt represented by the formula (I):

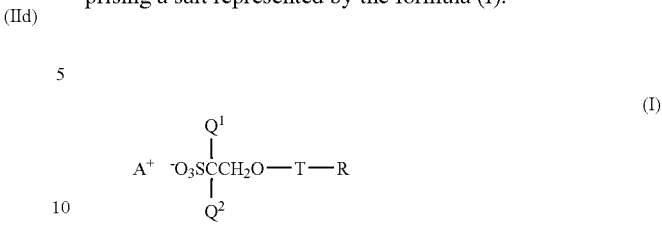
(I)

wherein $Q^1$ and $Q^2$ each independently represent a fluorine atom or a C1-C6 perfluoroalkyl group, T represents a methylene group or a carbonyl group, R represents an adamantyl group substituted with at least one selected from the group consisting of a C1-C4 alkyl group, a C1-C4 alkoxy group, a hydroxyl group, a hydroxymethyl group, a cyano group and an oxo group, and $A^+$ represents an organic counter ion, and a resin which contains a structural unit which has an acid-labile group and which itself is insoluble or poorly soluble in an aqueous alkali solution but becomes soluble in an aqueous alkali solution by the action of an acid;

<10> The chemically amplified positive resist composition according to <9>, wherein $Q^1$ and $Q^2$ each independently represent a fluorine atom or a trifluoromethyl group;

<11> The chemically amplified positive resist composition according to <9>, wherein $Q^1$ and $Q^2$ represent fluorine atoms;

<12> The chemically amplified positive resist composition according to any one of <9> to <11>, wherein the resin contains a structural unit derived from a monomer having a bulky and acid-labile group;

<13> The chemically amplified positive resist composition according to <12>, wherein the bulky and acid-labile group is a 2-alkyl-2-adamantyl ester group or a 1-(1-adamantyl)-1-alkylalkyl ester group;

<14> The chemically amplified positive resist composition according to <12>, wherein the monomer having a bulky and acid-labile group is 2-alkyl-2-adamantyl acrylate, 2-alkyl-2-adamantyl methacrylate, 1-(1-adamantyl)-1-alkylalkyl acrylate, 1-(1-adamantyl)-1-alkylalkyl methacrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate;

<15> The chemically amplified positive resist composition according to <12>, wherein the monomer having a bulky and acid-labile group is 2-alkyl-2-adamantyl acrylate, 2-alkyl-2-adamantyl methacrylate, 1-(1-adamantyl)-1-alkylalkyl acrylate and 1-(1-adamantyl)-1-alkylalkyl methacrylate;

<16> The chemically amplified positive resist composition according to <12>, wherein the monomer having a bulky and acid-labile group is 2-alkyl-2-adamantyl acrylate and 2-alkyl-2-adamantyl methacrylate;

<17> The chemically amplified positive resist composition according to any one of <9> to <16>, wherein the chemically amplified positive resist composition further comprises a basic compound.

DESCRIPTION OF PREFERRED EMBODIMENTS

The present invention provides a salt represented by the formula (I):

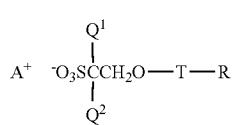

wherein $Q^1$ and $Q^2$ each independently represent a fluorine atom or a C1-C6 perfluoroalkyl group, T represents a methylene group or a carbonyl group, R represents an adamantyl group substituted with at least one selected from the group consisting of a C1-C4 alkyl group, a C1-C4 alkoxy group, a hydroxyl group, a hydroxymethyl group, a cyano group and an oxo group, and $A^+$ represents an organic counter ion (hereinafter, simply referred to as Salt (I)).

Examples of the C1-C6 perfluoroalkyl group include a trifluoromethyl, pentafluoroethyl, heptafluoropropyl, nonafluorobutyl undecafluoropentyl and tridecafluorohexyl group, and the trifluoromethyl group is preferable.

$Q^1$ and $Q^2$ each independently preferably represent the fluorine atom or the trifluoromethyl group. $Q^1$ and $Q^2$ represent the fluorine atoms more preferably.

Examples of the C1-C4 alkyl group include a methyl group, an ethyl group, an n-propyl group, an isopropyl group, an n-butyl group, a sec-butyl group and a tert-butyl group. Examples of the C1-C4 alkoxy group include a methoxy group, an ethoxy group, an n-propoxy group, an isopropoxy group, an n-butoxy group, a sec-butoxy group and a tert-butoxy group.

R preferably represents an adamantyl group substituted with a hydroxyl group or an oxo group.

Examples of the anion part of Salt (I) include the followings.

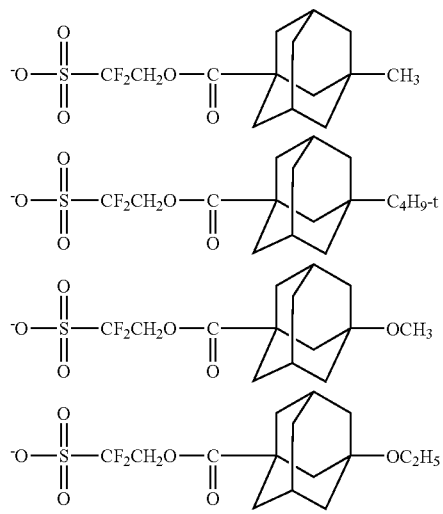

-continued

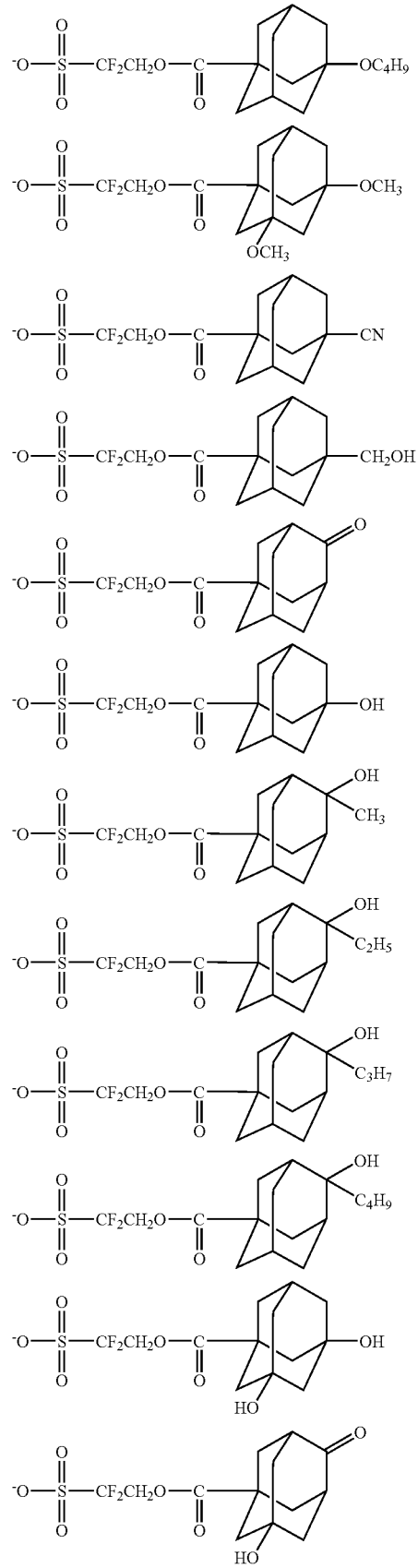

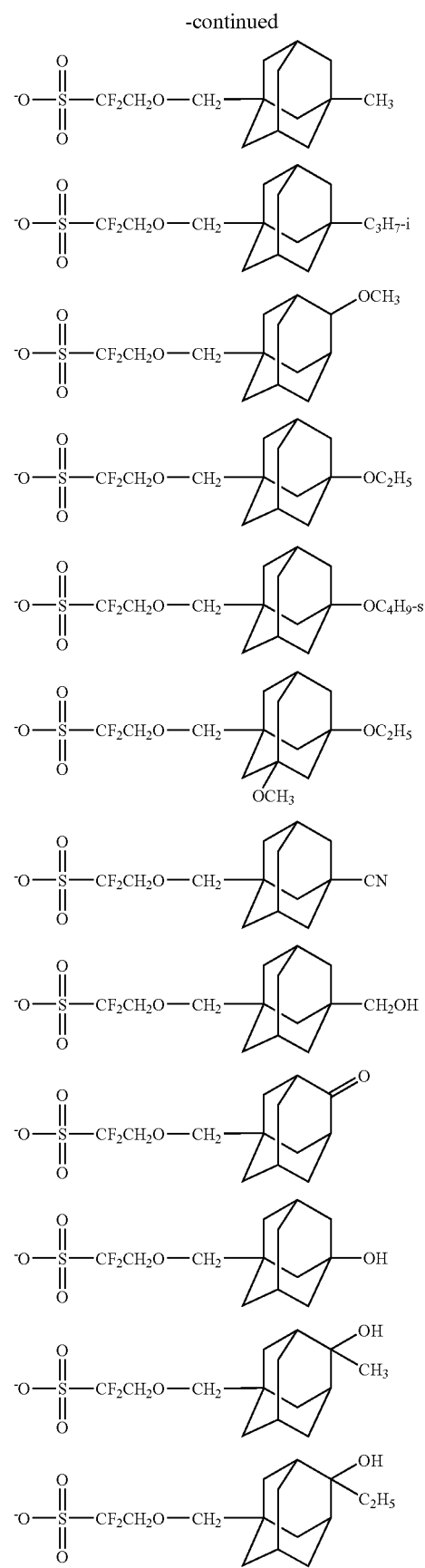
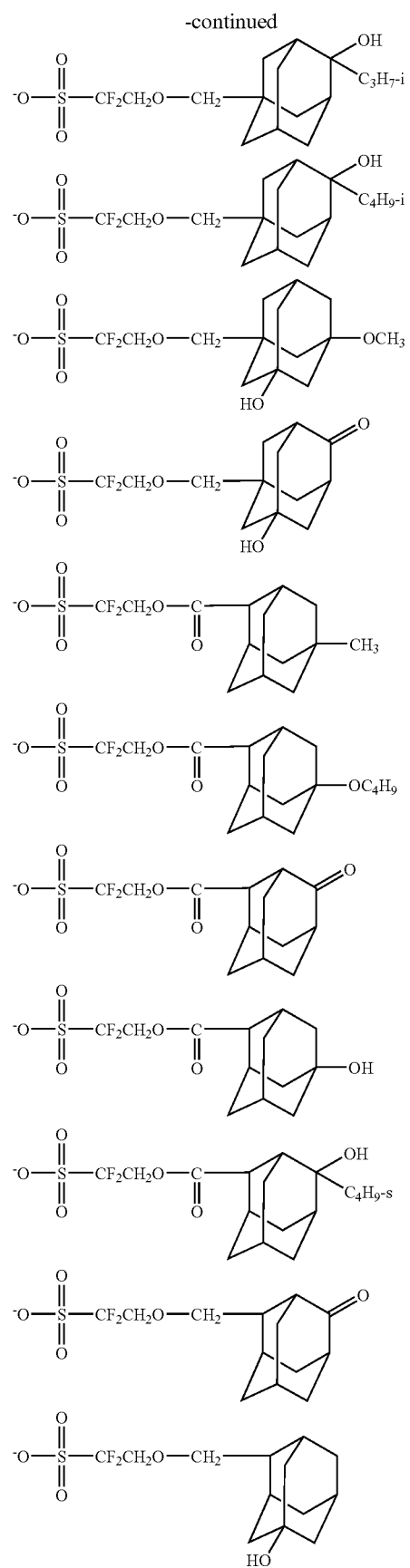

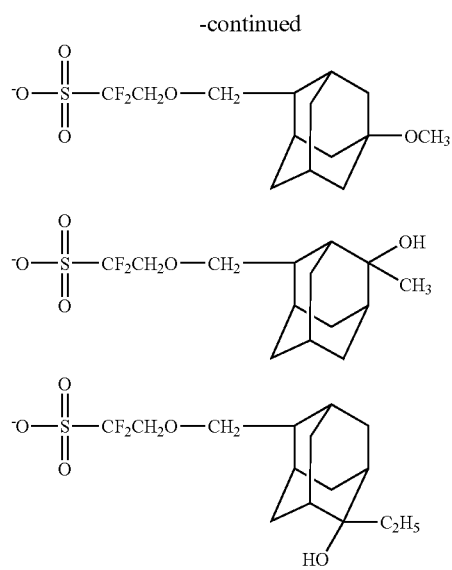
Among them, the following anion parts are preferable.
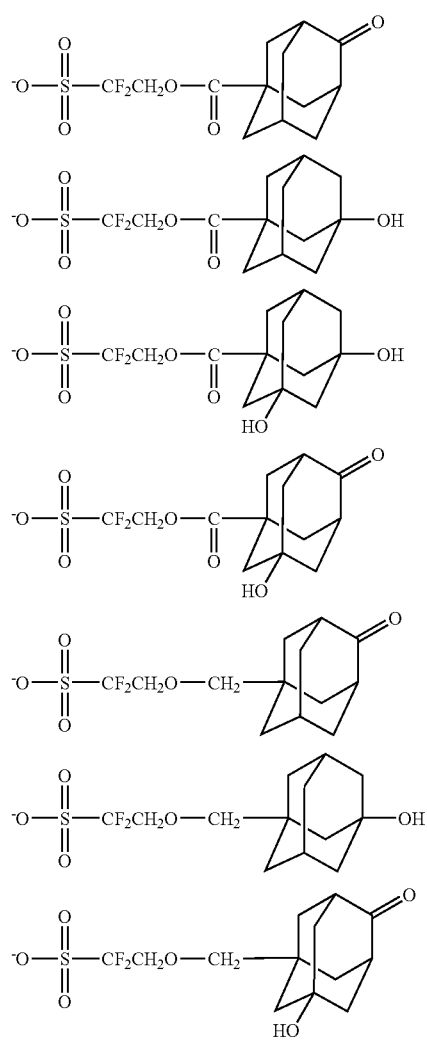
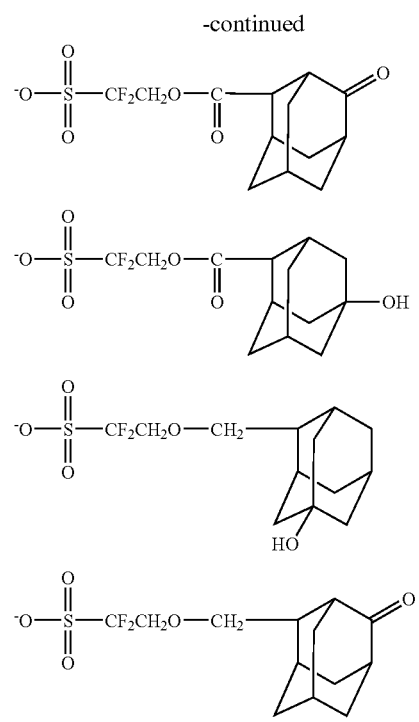
The following anion parts are more preferable.
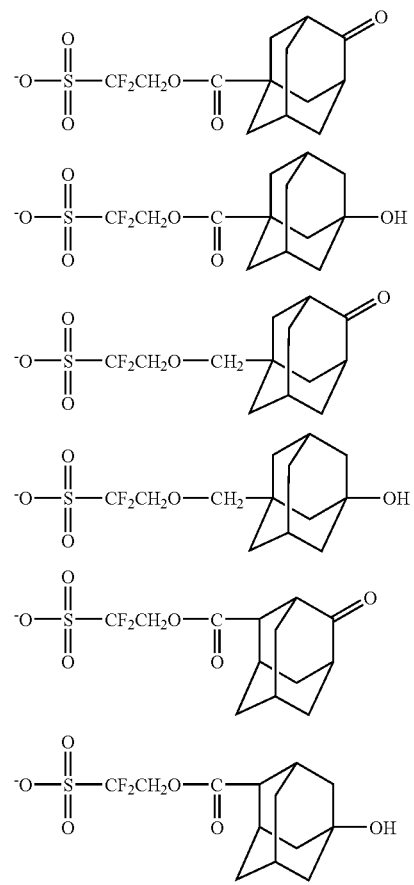

-continued

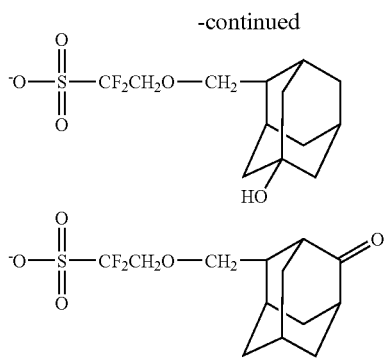

In the formula (I), A⁺ represents an organic counter ion.

Examples of the organic counter ion include a cation represented by the formula (IIa):

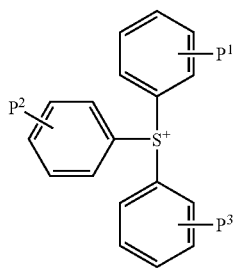

(IIa)

wherein $P^1$, $P^2$ and $P^3$ each independently represent a hydrogen atom, a hydroxyl group, a C1-C12 alkyl group or a C1-C12 alkoxy group, a cation represented by the formula (IIb):

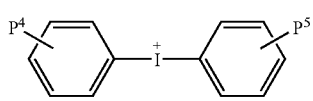

(IIb)

wherein $P^4$ and $P^5$ each independently represent a hydrogen atom, a hydroxyl group, a C1-C12 alkyl group or a C1-C12 alkoxy group, a cation represented by the formula (IIc):

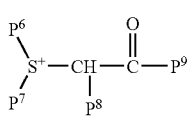

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent S⁺, and at least one —CH₂— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —CH₂— in the divalent acyclic hydrocarbon group may be substituted with —CO—, —O— or —S—, and a cation represented by the formula (IId):

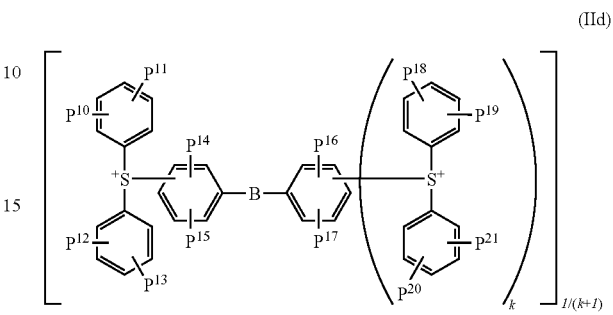

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

Examples of the C1-C12 alkyl group in the formulae (IIa), (IIb), (IIc) and (IId) include a methyl group, an ethyl group, an n-propyl group, an isopropyl group, an n-butyl group, an isobutyl group, a sec-butyl group, a tert-butyl group, an n-pentyl group, an n-hexyl group, an n-octyl group and a 2-ethylhexyl group.

Examples of the C1-C12 alkoxy group in the formulae (IIa), (IIb), (IIc) and (IId) include a methoxy group, an ethoxy group, an n-propoxy group, an isopropoxy group, an n-butoxy group, an isobutoxy group, a sec-butoxy group, a tert-butoxy group, an n-pentyloxy group, an n-hexyloxy group, an n-octyloxy group and a 2-ethylhexyloxy group.

Examples of the C3-C12 cycloalkyl group in the formula (IIc) include a cyclopropyl group, a cyclobutyl group, a cyclopentyl group, a cyclohexyl group, a cycloheptyl group, a cyclooctyl group and a cyclodecyl group.

Examples of the C3-C12 divalent acyclic hydrocarbon group formed by bonding $P^6$ and $P^7$ in the formula (IIc) include a trimethylene group, a tetramethylene group and a pentamethylene group. Examples of the ring group formed together with the adjacent S⁺ and the divalent acyclic hydrocarbon group include a tetramethylenesulfonio group, a pentamethylenesulfonio group and an oxybisethylenesulfonio group.

Examples of the aromatic group in the formula (IIc) include a phenyl group, a tolyl group, a xylyl group and a naphthyl group. Examples of the divalent acyclic hydrocarbon group formed by bonding $P^8$ and $P^9$ in the formula (IIc) include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

The cation represented by the formula (IIa) or (IIc) is preferable and the cation represented by the formula (IIa) is more preferable.

Examples of the cation represented by the formula (IIa) include the followings:

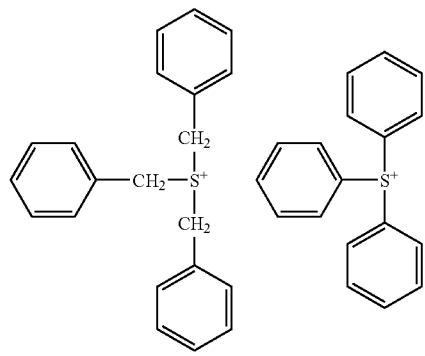
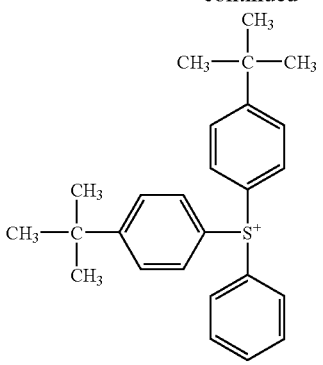
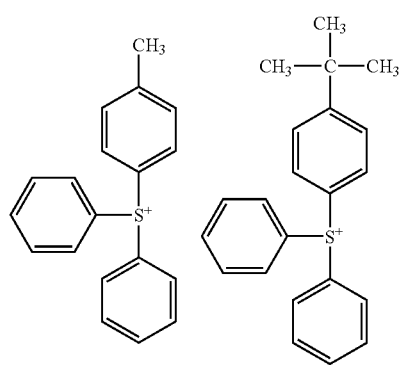
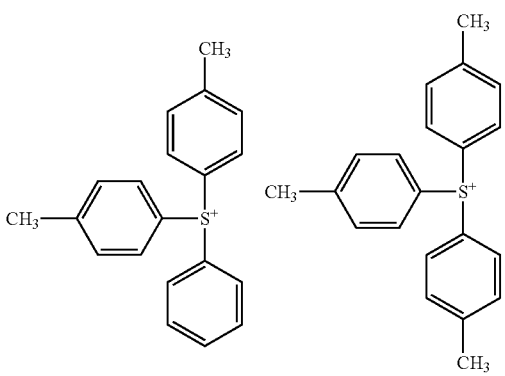
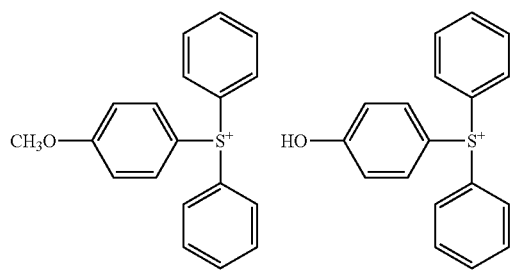
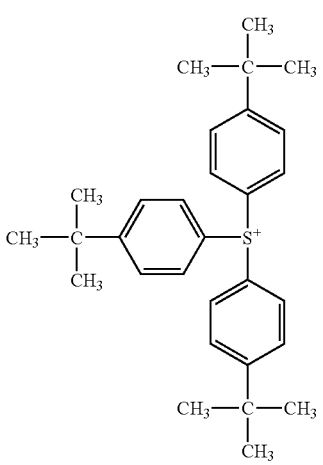
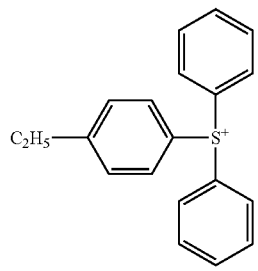
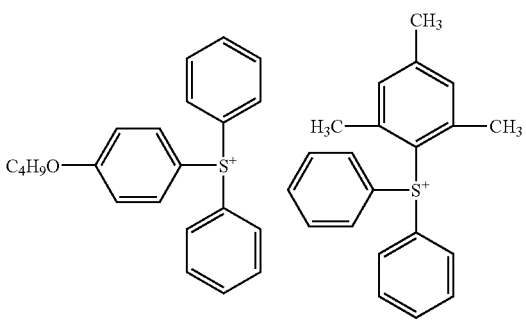
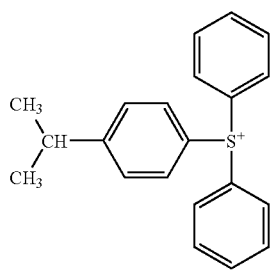

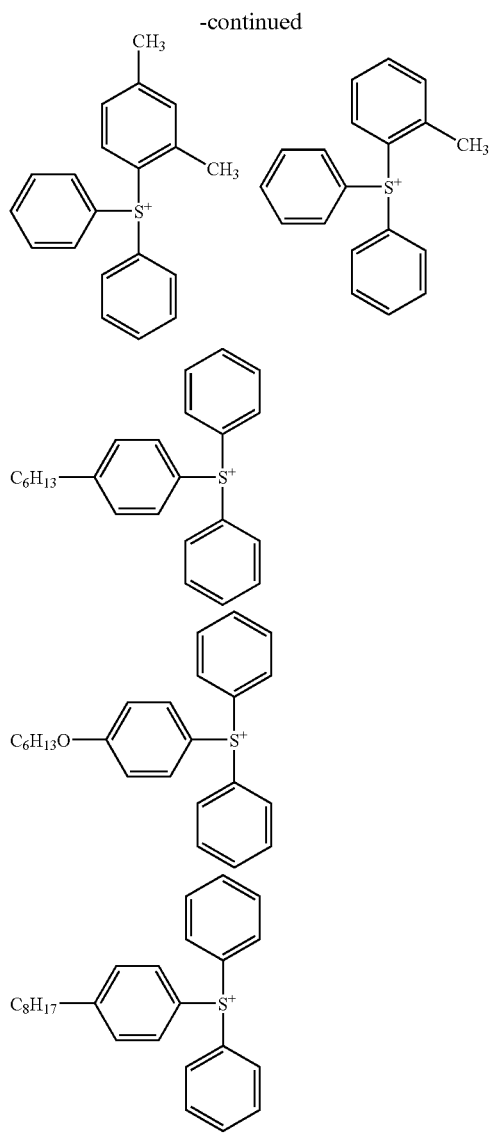
Examples of the cation represented by the formula (IIb) include the followings:
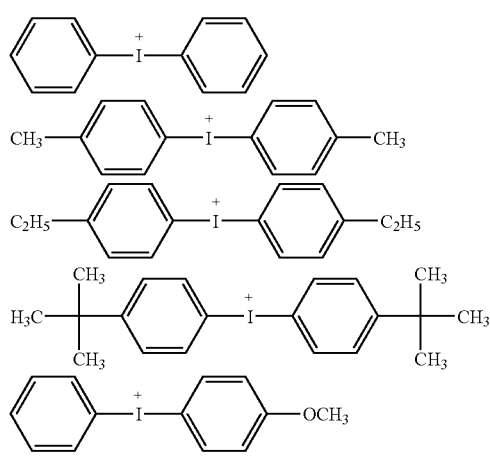
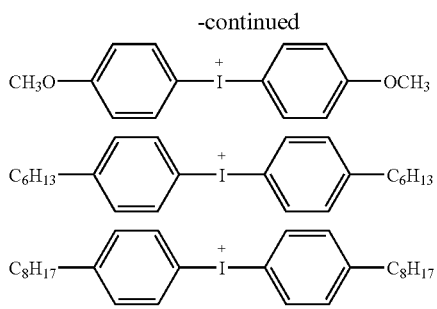
Examples of the cation represented by the formula (IIc) include the followings:
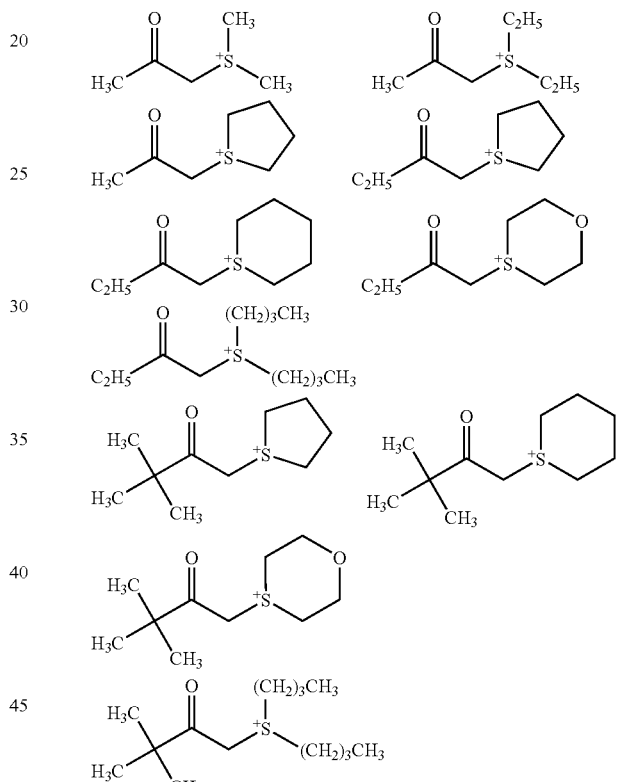
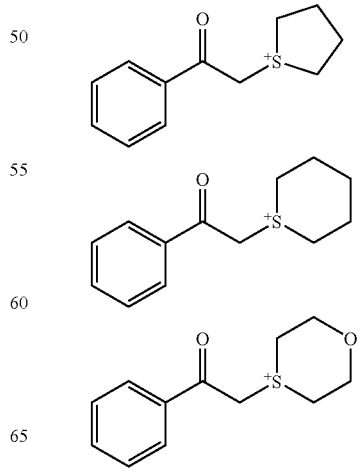

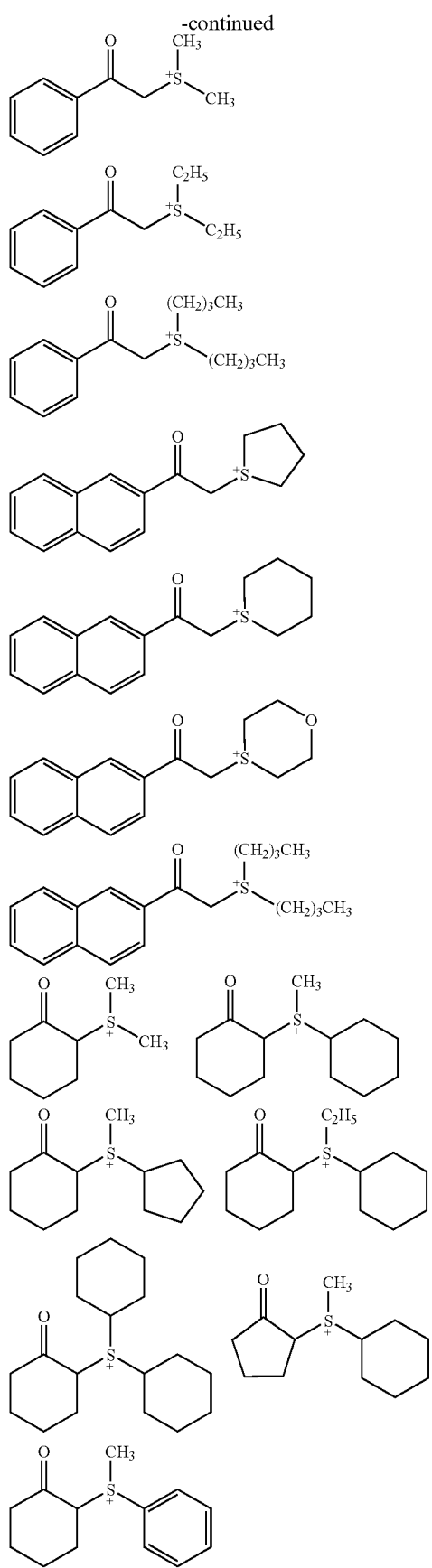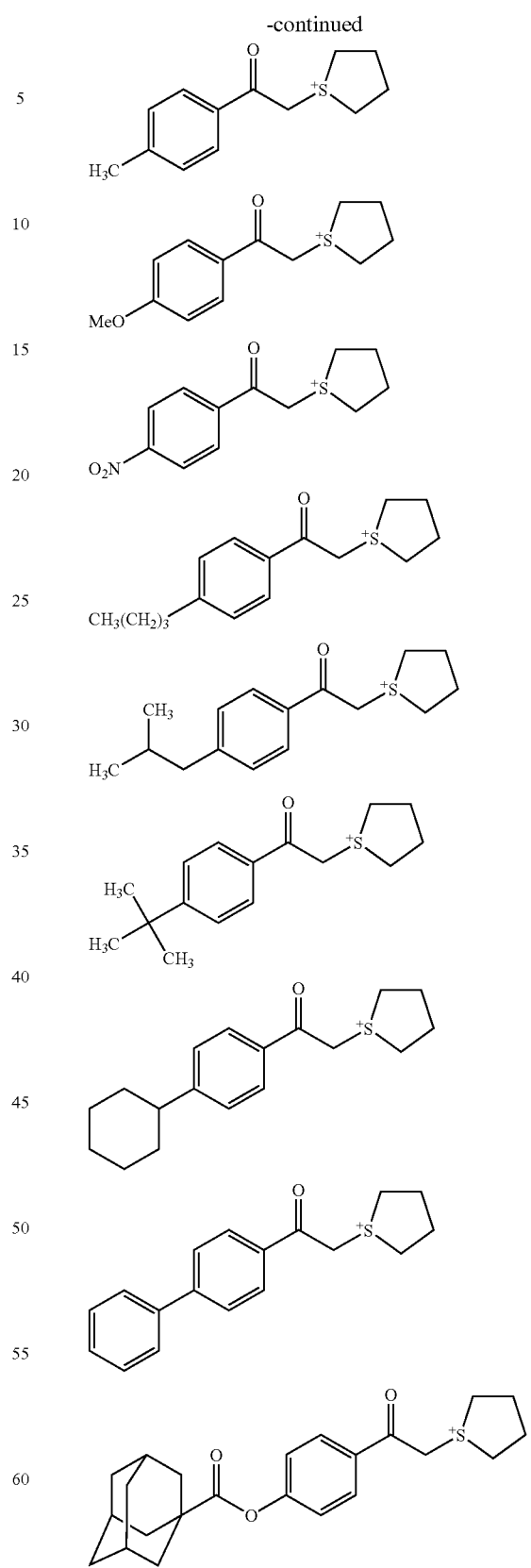
Examples of the cation represented by the formula (IId) include the followings.

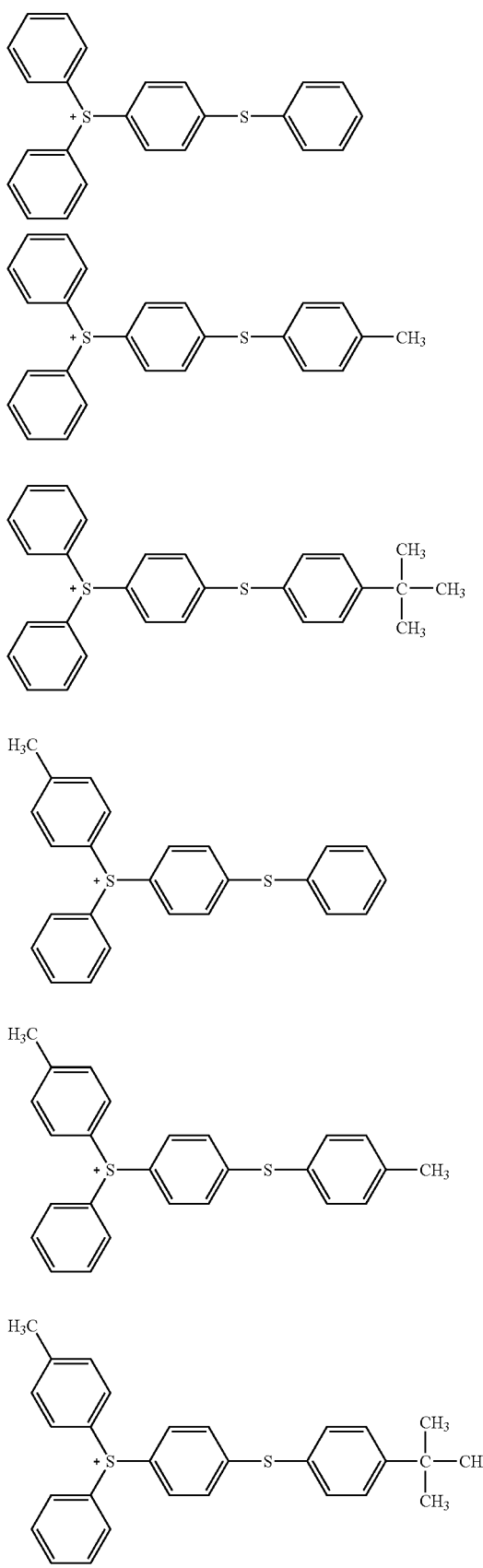
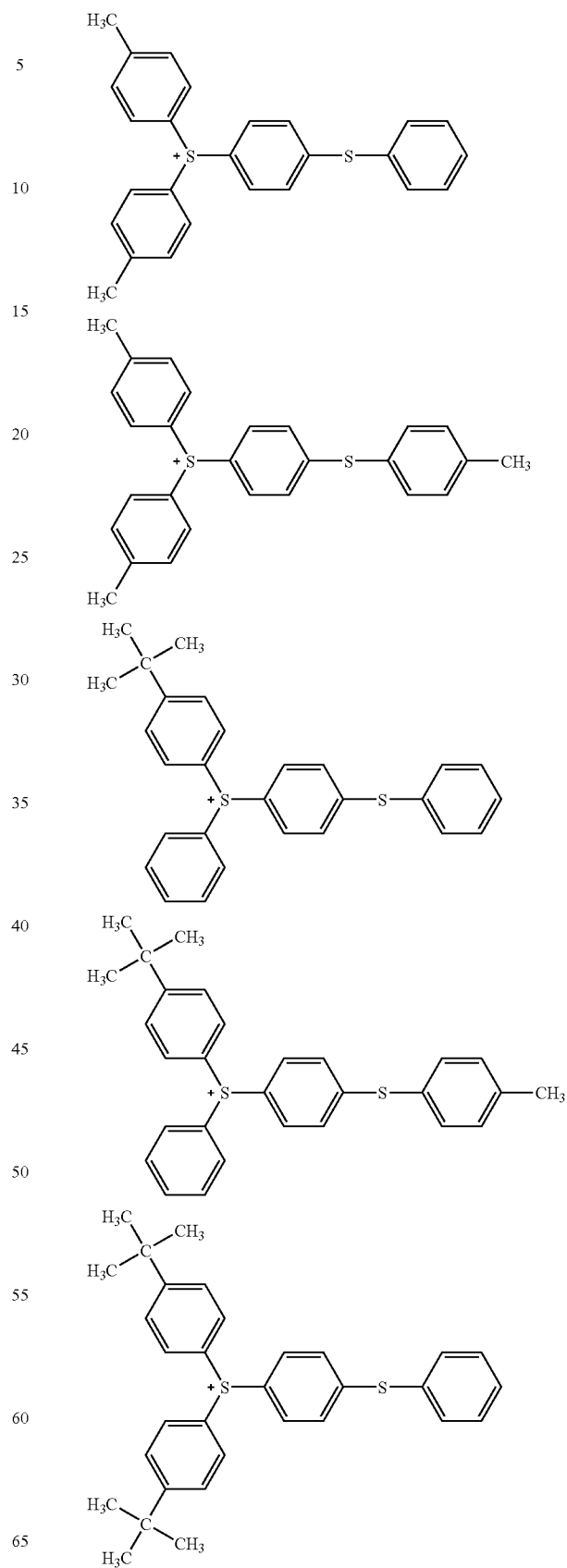
-continued

-continued
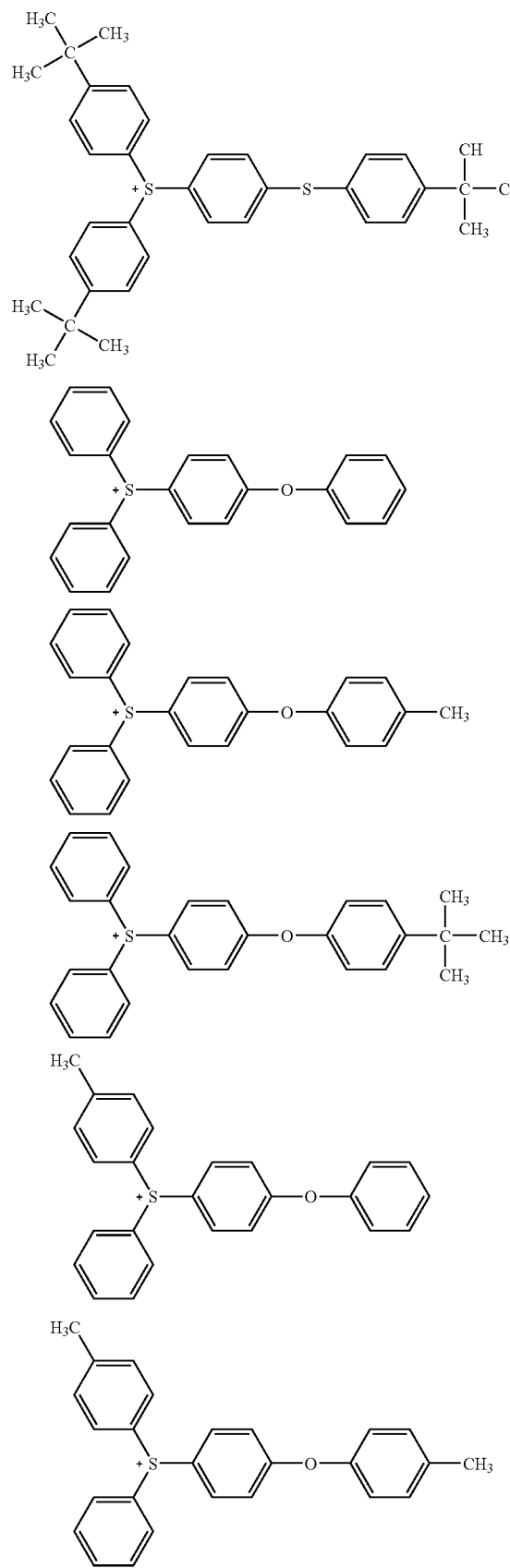
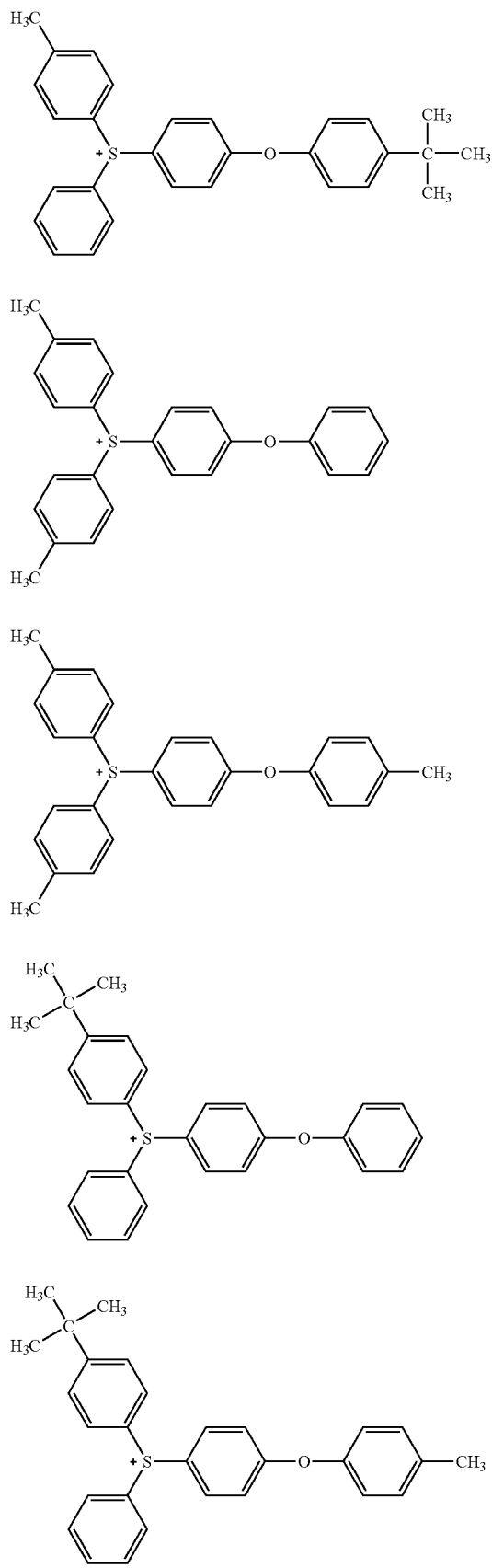

-continued
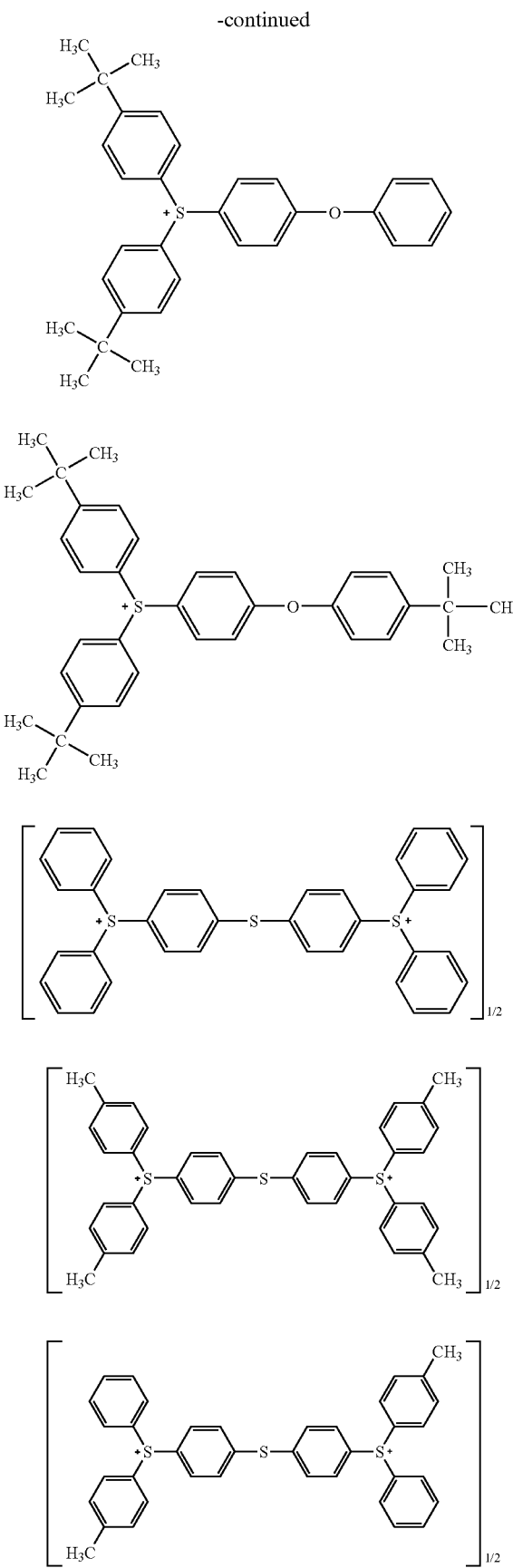
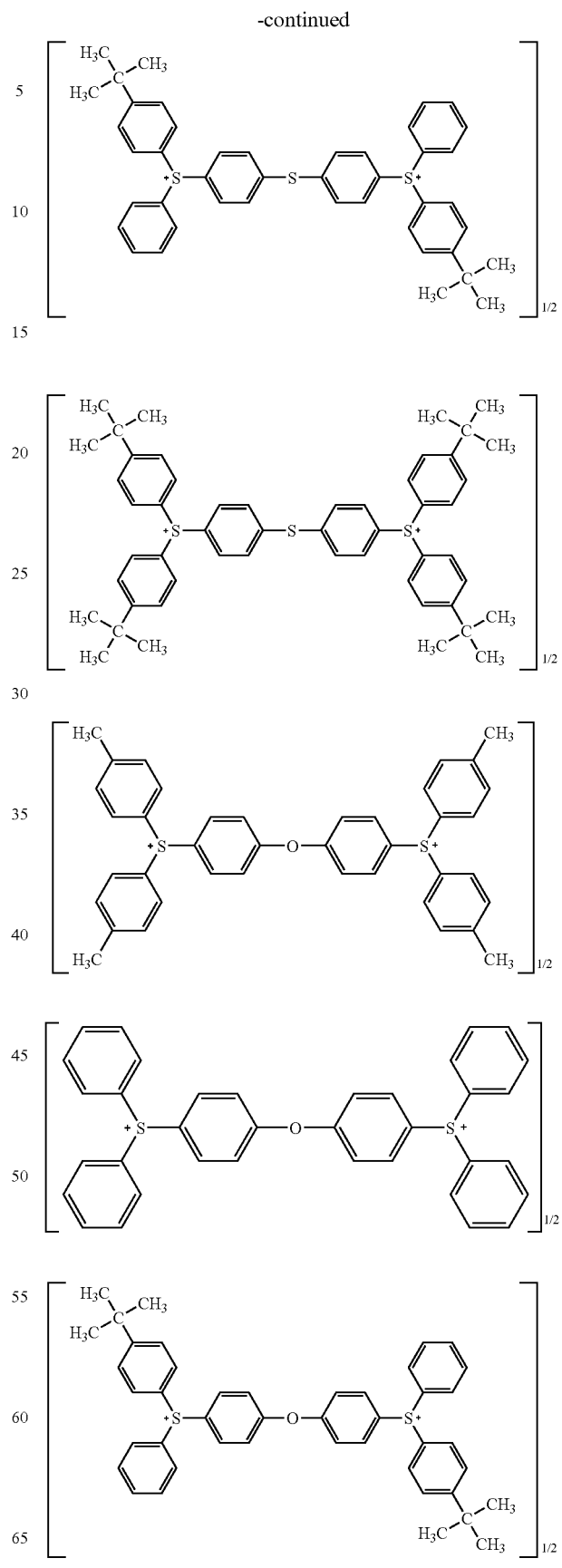

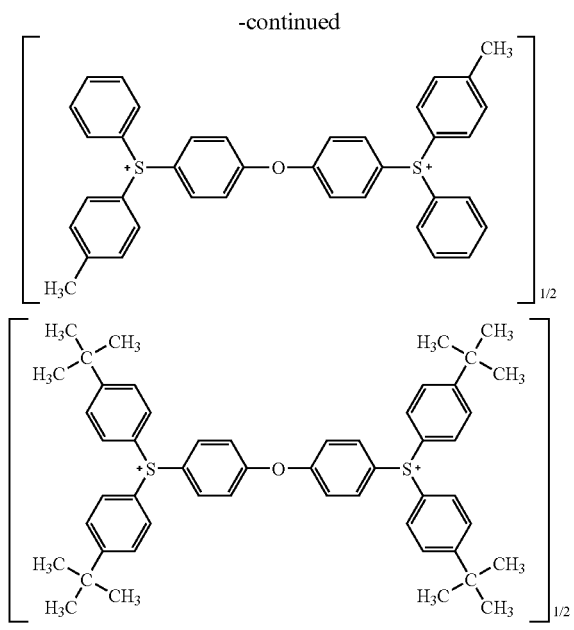

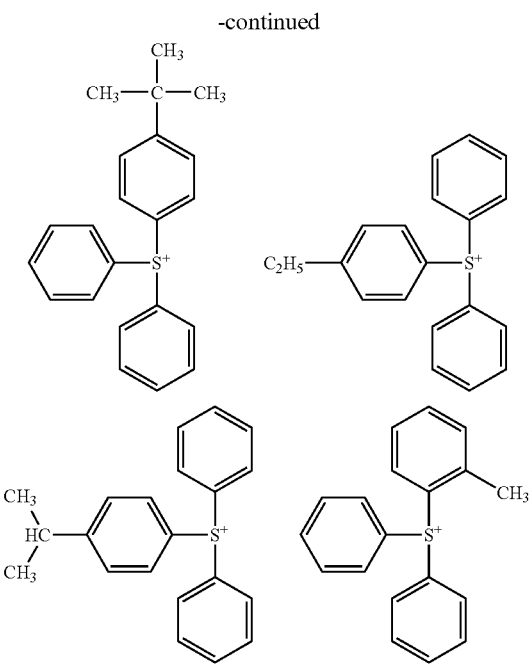

As the organic counter ion, a cation represented by the formula (IIe):

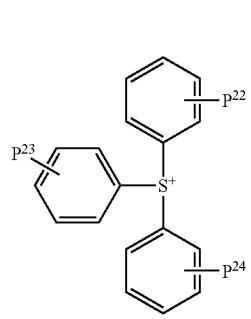

(IIe)

wherein $P^{22}$, $P^{23}$ and $P^{24}$ each independently represent a hydrogen atom or a C1-C4 alkyl group, is preferable.

Examples of the C1-C4 alkyl group in the formula (IIe) include a methyl group, an ethyl group, an n-propyl group, an isopropyl group, an n-butyl group, an isobutyl group, a sec-butyl group and a tert-butyl group.

Examples of the cation represented by the formula (IIe) include the followings:

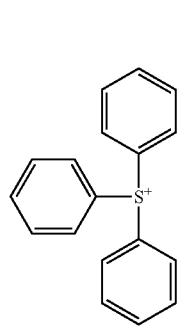
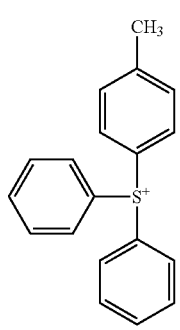
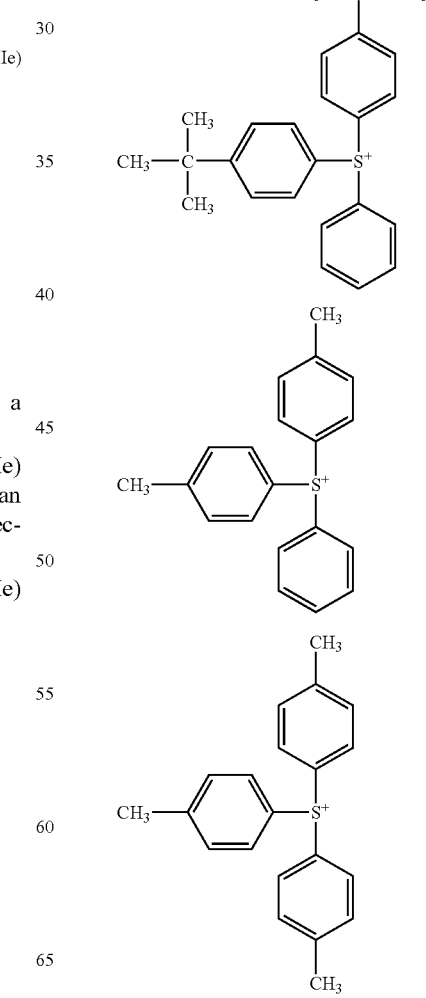

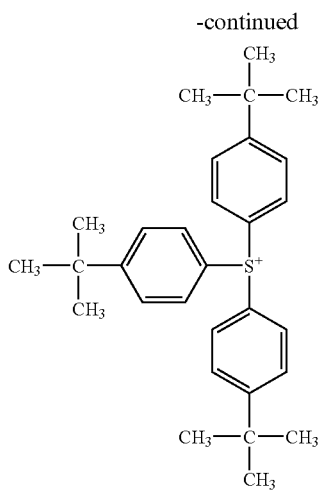

As Salt (I), the salts represented by the following formulae (IIIa), (IIIb), (IIIc) and (IIId) are preferable for providing chemically amplified resist compositions giving patterns having excellent pattern shape.

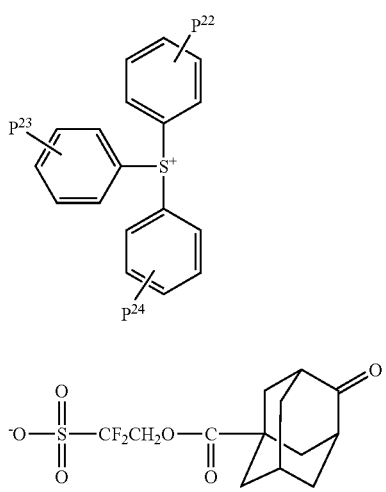

(IIIa)

(IIIb)

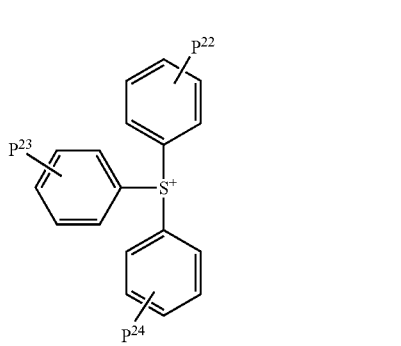

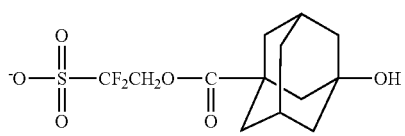

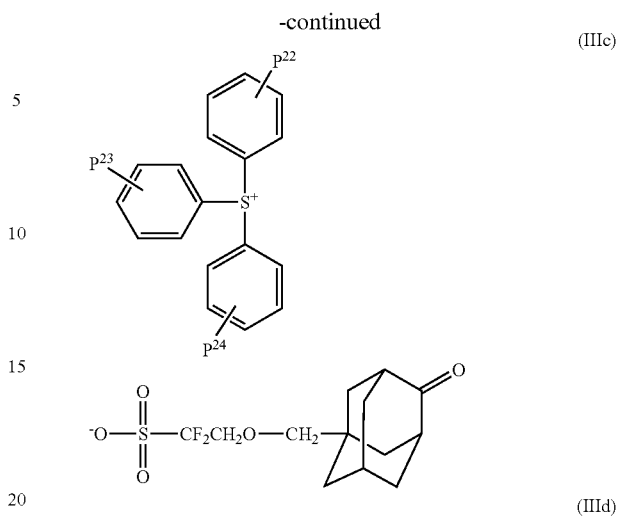

(IIIc)

(IIId)

As Salt (I), the salts represented by the formulae (IIIa) and (IIIb) are more preferable.

Examples of the process for production of Salt (I) include a process comprising reacting a salt represented by the formula (V):

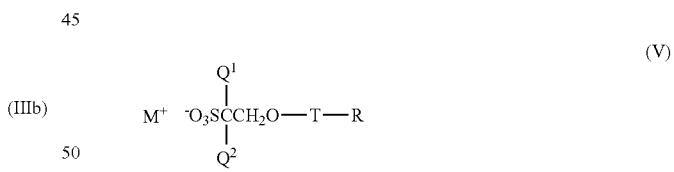

(V)

wherein $Q^1$, $Q^2$, T and R are the same as defined above, and M represents Li, Na, K or Ag (hereinafter, simply referred to as the salt (V)), with a compound represented by the formula (XI):

A⁺Z⁻ (XI)

wherein A⁺ is the same as defined above and Z represents F, Cl, Br, I, $BF_4$, $AsF_6$, $SbF_6$, $PF_6$ or $ClO_4$ (hereinafter, simply referred to as the compound (XI)), in an inert solvent such as acetonitrile, water, methanol, chloroform and dichloromethane, at a temperature of 0 to 150° C., preferably of 0 to 100° C. Two or more inert solvents may be mixed to use.

As the compound (XI), commercially available one is usually used.

The used amount of the compound (XI) is usually 0.5 to 2 moles per 1 mole of the salt (V). Salt (I) obtained may be taken out by crystallization or washing with water.

The salt (V) can be produced by a process comprising reacting a compound represented by the formula (VI):

HO-T-R (VI)

wherein T and R are the same as the defined above (hereinafter, simply referred to as the compound (VI)), with a salt represented by the formula (IX):

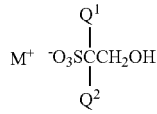

$$M^+ \quad ^-O_3SCCH_2OH \quad \begin{array}{c} Q^1 \\ | \\ | \\ Q^2 \end{array}$$ (IX)

wherein $Q^1$, $Q^2$, T, R and M are the same as defined above (hereinafter, simply referred to as the salt (IX)).

The reaction of the compound (VI) and the salt (IX) is usually conducted by mixing both in an aprotic solvent such as dichloroethane, toluene, ethylbenzene, monochlorobenzene, acetonitrile and N,N-dimethylformamide, at 20 to 200° C., preferably 50 to 150° C. The reaction is usually conducted in the presence of an acid catalyst. Examples of the acid catalyst include an organic acid such as p-toluenesulfonic acid and an inorganic acid such as sulfuric acid.

The reaction is preferably conducted while removing the alcohol compound generated, for example, by Dean Stark method as the reaction time tends to be shortened. The reaction may be conducted in the presence of a dehydrating agent. Examples of the dehydrating agent include 1,1'-carbonyldiimidazole, N,N'-dicyclohexylcarbodiimide, a 1-alkyl-2-halopyridinium salt, bis(2-oxo-3-oxazolidinyl)phosphinic chloride, 1-ethyl-3-(3-dimethylaminopropyl)carbodiimide hydrochloride, di-2-pyridyl carbonate, di-2-pyridyl thionocarbonate and 6-methyl-2-nitrobenzoic anhydride/4-(dimethylamino)pyridine.

The used amount of the salt (IX) is usually 0.5 to 3 moles, preferably 1 to 2 moles per 1 mole of the compound (VI). The used amount of the acid catalyst is usually 0.001 to 5 moles per 1 mole of the compound (VI). The used amount of the dehydrating agent is usually 0.5 to 5 moles per 1 mole of the compound (VI) and preferably 1 to 3 moles.

When a compound represented by the formula (VIa):

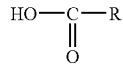

$$HO-\underset{\underset{O}{\parallel}}{C}-R$$ (VIa)

wherein R is the same as the defined above (hereinafter, simply referred to as the compound (VIa)) is used as the compound (VI), the salt (V) wherein T is a carbonyl group can be also produced by reacting the compound (VIa) with a halogenating agent to prepare the corresponding acid halide compound and reacting the corresponding acid halide compound with the salt (IX).

Examples of the halogenating agent include thionyl chloride, thionyl bromide, phosphorous trichloride, phosphorous pentachloride and phosphorous tribromide. The reaction of the compound (VIa) and the halogenating agent is usually conducted by mixing both in an inert solvent such as an aprotic solvent (e.g. dichloroethane, toluene, ethylbenzene, monochlorobenzene, N,N-dimethylformaide, etc.) at 20 to 200° C., preferably 50 to 150° C. The reaction is usually conducted in the presence of an amine compound.

The reaction of the corresponding acid halide compound and the salt (IX) is usually conducted by mixing both in an inert solvent such as an aprotic solvent (e.g. dichloroethane, toluene, ethylbenzene, monochlorobenzene, N,N-dimethylformaide, etc.) at 20 to 200° C., preferably 50 to 150° C. The reaction is preferably conducted in the presence of a base. Examples of the base include an organic base such as triethylamine and pyridine, and an inorganic base such as sodium hydroxide, potassium carbonate and sodium hydride. The used amount of the base is usually 0.001 to 5 moles per 1 mole of the corresponding acid halide compound, and preferably 1 to 3 moles.

When a compound represented by the formula (VIb):

HO—CH$_2$—R (VIb)

wherein R is the same as the defined above (hereinafter, simply referred to as the compound (VIb)) is used as the compound (VI), the salt (V) wherein T is a methylene group can be also produced by converting the compound (VI) into a compound represented by the formula (VIc):

L-CH$_2$—R (VIc)

wherein R is the same as the defined above and L represents a chlorine atom, a bromine atom, an iodine atom, a methanesulfonyloxy group, a p-toluenesulfonyloxy group or a trifluoromethanesulfonyloxy group (hereinafter, simply referred to as the compound (VIc)), and reacting the compound (VIc) with the salt (IX).

The compound (VIc) can be produced by reacting the compound (VIb) with thionyl chloride, thionyl bromide, phosphorous trichloride, phosphorous pentachloride, phosphorous tribromide, mesyl chloride, tosylchloride or trifluoromethanesulfonic anhydride, in an inert solvent such as an aprotic solvent (e.g. dichloroethane, toluene, ethylbenzene, monochlorobenzene, N,N-dimethylformaide, etc.) at −70 to 200° C., preferably −50 to 150° C. The reaction is preferably conducted in the presence of a base. Examples of the base include an organic base such as triethylamine and pyridine, and an inorganic base such as sodium hydroxide, potassium carbonate and sodium hydride. The used amount of the base is usually 0.001 to 5 moles per 1 mole of the compound (VIb), and preferably 1 to 3 moles.

The reaction of the compound (VIc) and the salt (IX) is usually conducted by mixing both in an inert solvent such as an aprotic solvent (e.g. dichloroethane, toluene, ethylbenzene, monochlorobenzene, N,N-dimethylformaide, etc.) at 20 to 200° C., preferably 50 to 150° C. The reaction is usually conducted in the presence of a base. Examples of the base include an organic base such as triethylamine and pyridine, and an inorganic base such as sodium hydroxide, potassium carbonate and sodium hydride. The used amount of the base is usually 0.001 to 5 moles per 1 mole of the corresponding acid halide compound, and preferably 1 to 3 moles.

The salt (V) can also be produced by reacting the compound (VI) with a compound represented by the formula (X):

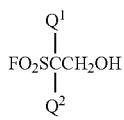

(X)

wherein $Q^1$ and $Q^2$ are the same as defined above (hereinafter, simply referred to as the compound (X)) followed by reacting with MOH (e.g. LiOH, NaOH, KOH, AgOH).

The salt (IX) can be produced by a process comprising hydrogenating a compound represented by the formula (XI):

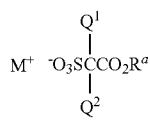

(XI)

wherein $Q^1$, $Q^2$ and M are the same as defined above and $R^a$ represents a C1-C4 alkyl group with LiAlH$_4$.

Next, the present chemically amplified positive resist composition will be illustrated.

The present chemically amplified positive resist composition comprises Salt (I) and a resin containing a structural unit which has an acid-labile group and which itself is insoluble or poorly soluble in an aqueous alkali solution but becomes soluble in an aqueous alkali solution by the action of an acid.

Salt (I) is usually used as an acid generator, and the acid generated by irradiation to Salt (I) catalytically acts against acid-labile groups in the resin, cleaves acid-labile groups, and the resin becomes soluble in an alkali aqueous solution. Such a composition is suitable for chemically amplified positive resist composition.

The resin used for the present composition contains a structural unit which has the acid-labile group and which itself is insoluble or poorly soluble in an alkali aqueous solution, but the acid-labile group cleave by an acid.

In the present specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethylester, 1-isopropoxyethylester, 1-ethoxypropoxyester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group), since excellent resolution is obtained when the resin obtained is used in the present composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present composition, a resist composition having excellent sensitivity and heat resistance tends to be obtained. In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin used for the present composition can also contain other structural unit or units derived from an acid-stable monomer in addition to the above-mentioned structural units having the acid-labile group. Herein, the "structural unit derived from an acid-stable monomer" means "a structural unit not dissociated by an acid generated from Salt (I)".

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (A):

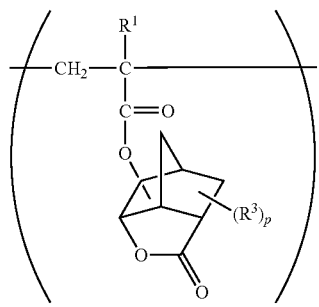

wherein $R^1$ represents a hydrogen atom or a methyl group, $R^3$ represents a methyl group, a trifluoromethyl group or a halogen atom, p represents an integer of 0 to 3, and when p represents 2 or 3, $R^3$s may be the same or different each other;

a structural unit represented by the formula (B):

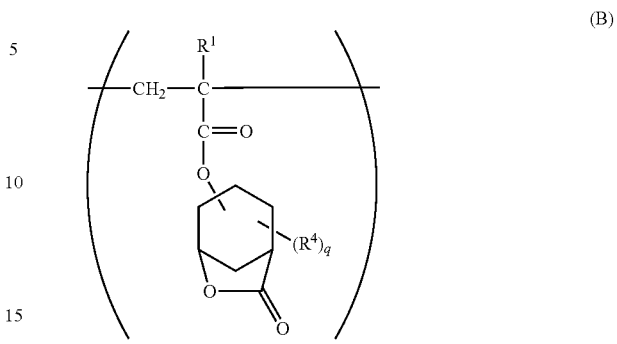

wherein $R^2$ represents a hydrogen atom or a methyl group, $R^4$ represents a methyl group, a trifluoromethyl group or a halogen atom, q represents an integer of 0 to 3, and when q represents 2 or 3, $R^4$s may be the same or different each other;

a structural unit derived from p-hydroxystyrene;

a structural unit derived from m-hydroxystyrene;

a structural unit derived from an alicyclic compound having an olefinic double bond such as a structural unit represented by the formula (C):

wherein $R^5$ and $R^6$ each independently represents a hydrogen atom, a C1-C3 alkyl group, a C1-C3 hydroxyalkyl group, a carboxyl group, a cyano group or a —COOU group in which U represents an alcohol residue, or $R^5$ and $R^6$ can be bonded together to form a carboxylic anhydride residue represented by —C(=O)OC(=O)—;

a structural unit derived from an aliphatic unsaturated dicarboxylic anhydride such as a structural unit represented by the formula (D):

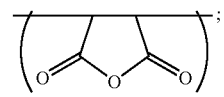

a structural unit represented by the formula (E):

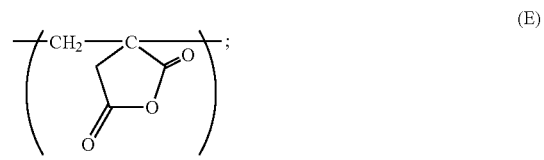

and the like.

Particularly, the resin having further at least one structural unit selected from the group consisting of the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit derived from α-acryloyloxy-γ-butyrolactone, the structural unit derived from α-methacryloyloxy-γ-butyrolactone, the structural unit derived from β-acryloyloxy-γ-butyrolactone, the structural unit derived from β-methacryloyloxy-γ-butyrolactone, the structural unit represented by the formula (A) and the structural unit represented by the formula (B) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone having the lactone ring which may be substituted with the alkyl group can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

As monomers to give structural units represented by the formulae (A) and (B), specifically listed are, for example, an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

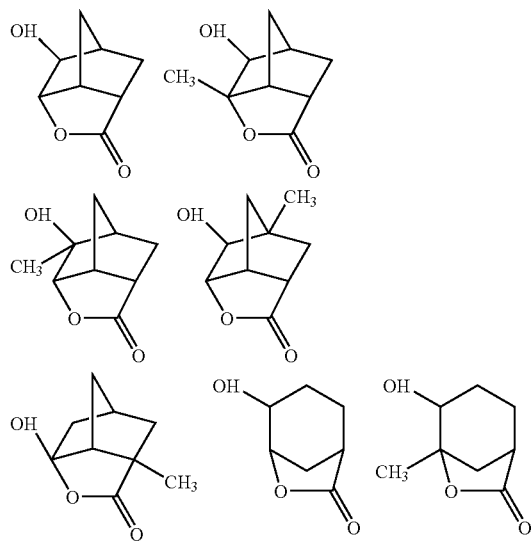

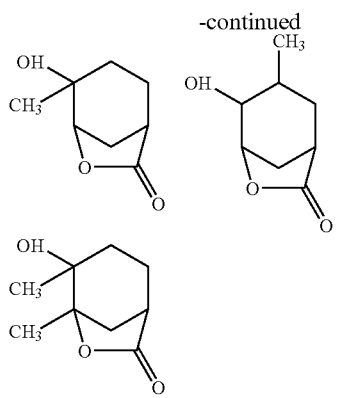

Examples of the acryloyloxy-γ-butyrolactone and the methacryloyloxy-γ-butyrolactone having the lactone ring which may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (C). The structural unit derived from maleic anhydride and from itaconic anhydride which are the structural unit derived from aliphatic unsaturated dicarboxylic anhydrides are formed by opening of their double bonds, and can be represented by the above-mentioned formula (D) and the formula (E), respectively.

In $R^5$ and $R^6$, examples of the C1-C3 alkyl group include a methyl, ethyl, and n-propyl group, and examples of the C1-C3 hydroxyalkyl group include a hydroxymethyl and 2-hydroxyethyl group.

In $R^5$ and $R^6$, the —COOU group is an ester formed from the carboxyl group, and as the alcohol residue corresponding to U, for example, an optionally substituted C1-C8 alkyl group, 2-oxooxolan-3-yl group, 2-oxooxolan-4-yl and the like are listed, and as the substituent on the C1-C8 alkyl group, a hydroxyl group, an alicyclic hydrocarbon residue and the like are listed.

Specific examples of the monomer used to give the structural unit represented by the above-mentioned formula (C) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (C) is a structural unit having the acid-labile group even if it has the norbornene structure. Examples of monomers giving structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, and the like.

The resin used in the present composition preferably contains the structural unit or units having the acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of the structural units is 15% by mole or more in all structural units of the resin.

When, in addition to structural units having the acid-labile group, other structural units having the acid-stable group are contained in the resin, it is preferable that the sum of these structural units is in the range of 20 to 90% by mole based on all structural units of the resin.

The resin used for the present composition can be produced by conducting polymerization reaction of the corresponding monomer or monomers. The resin can be also produced by conducting oligomerization of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable, and 2,2'-azobisisobutyronitrile and 2,2'-azobis(2,4-dimethylvaleronitrile) are especially preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After completion of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The present resist composition preferably includes 80 to 99.9% by weight of the resin component and 0.1 to 20% by weight of Salt (I) based on the total amount of the resin component and Salt (I).

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

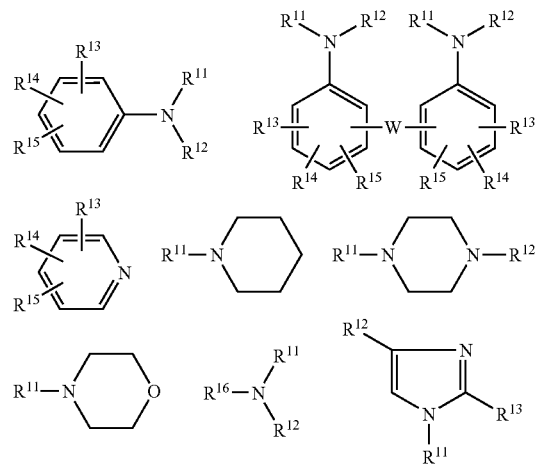

-continued

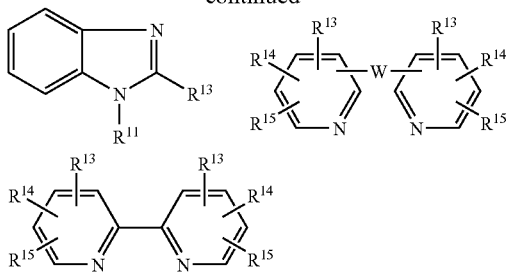

wherein $R^{11}$ and $R^{12}$ independently represent a hydrogen atom, an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy group may be substituted with at least one group selected from a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy group which may be substituted with at least one group selected from a hydroxyl group, an amino group which may be substituted with a C1-C4 alkyl group and a C1-C6 alkoxy group, $R^{16}$ represents an alkyl or cycloalkyl group, and the alkyl and cycloalkyl group may be substituted with at least one group selected from a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

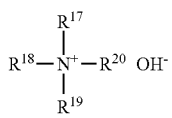

wherein $R^{17}$, $R^{18}$, $R^{19}$ and $R^{20}$ independently represent an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group.

The alkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The aryl group in $R^{11}$, $R^{12}$, $R^{13}$, $R^{14}$, $R^{15}$, $R^{17}$, $R^{18}$, $R^{19}$ and $R^{20}$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The alkoxy group in $R^{13}$, $R^{14}$ and $R^{15}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and Salt (I).

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted. The weight-average molecular weight of any material in the following Examples is a value found by gel permeation chromatography [HLC-8120GPC Type, Column (Total 3 Columns): TSKgel Multipore HXL-M manufactured by TOSOH CORPORATION, Solvent: tetrahydrofuran] using polystyrene as a standard reference material.

Structures of salts obtained were determined by NMR (GX-270 Type or EX-270 Type, manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

Salt Synthesis Example 1

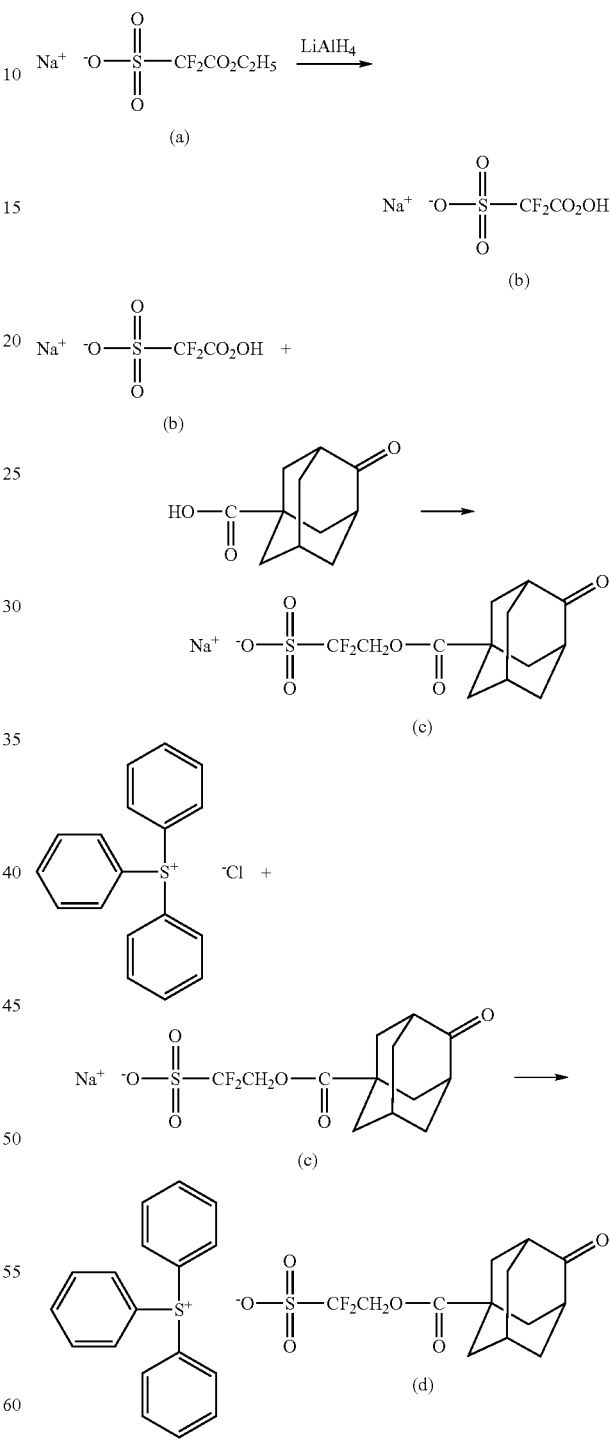

(1) Ten point four grams of lithium aluminum hydride was mixed with 120 mL of anhydrous tetrahydrofuran. To the resultant mixture, a solution prepared by mixing 62.2 g of a salt of the above-mentioned formula (a) with 900 mL of anhydrous tetrahydrofuran was added dropwise in an ice bath (below 7° C.). The resultant mixture was stirred at room temperature for 5 hours. Ethyl acetate was added to the obtained mixture to decompose excess lithium aluminum hydride and then 50 mL of 6N hydrochloric acid was added dropwise to the resultant mixture. The obtained mixture was concentrated. The obtained residue was purified with silica gel chromatography (chloroform/methanol=5/1) to obtain 84.7 g of the salt of the above-mentioned formula (b) (content: 60%). $^1$H-NMR (dimethylsulfoxide-d$_6$, Internal standard: tetramethylsilane): δ (ppm) 3.81 (m, 2H), 5.28 (t, 1H, J=6.2 Hz)

$^{13}$C-NMR (dimethylsulfoxide-d$_6$): δ (ppm) 120.5 (t, J=276 Hz), 60.1

$^{19}$F-NMR (dimethylsulfoxide-d$_6$, Internal standard: fluorobenzene): δ (ppm) 111.9

(2) Four point five grams of 4-oxoadamantane-1-carboxylic acid was dissolved in 90 mL of anhydrous tetrahydrofuran. To the obtained solution, a solution prepared by mixing 3.77 g of 1,1'-carbonyldiimidazole with 45 mL of anhydrous tetrahydrofuran was added dropwise at room temperature. The resultant mixture was stirred at room temperature for 4 hours. The mixture was added dropwise to a mixture of 7.87 g of the salt of the above-mentioned formula (b) obtained in the above-mentioned (1) and 50 mL of anhydrous tetrahydrofuran at 54 to 60° C. over 0.5 hours. The resultant mixture was refluxed for 18 hours. After cooling, the reaction mixture was filtrated to remove insoluble matters and insoluble matters were washed with chloroform. The obtained filtrate was concentrated to obtain 10.36 g of the residue. The residue was purified with silica gel chromatography (chloroform/methanol) to obtain 4.97 g of the salt of the above-mentioned formula (c) (yield: 59.4%).

$^1$H-NMR (dimethylsulfoxide-d$_6$, Internal standard: tetramethylsilane): δ (ppm) 1.89-1.92 (m, 2H), 2.02-2.04 (m, 2H), 2.07-2.18 (m, 7H), 2.46 (s, 2H), 4.57 (t, 2H, J=15.3 Hz)

$^{19}$F-NMR (dimethylsulfoxide-d$_6$, Internal standard: fluorobenzene): δ (ppm) 110.6

(3) One gram of the salt of the above-mentioned formula (c) obtained in the above-mentioned (2) was dissolved in 20 g of chloroform. To the solution, 6.3 g of aqueous triphenylsulfonium chloride solution (concentration: 13.1%) was added at room temperature. The resultant mixture was stirred at room temperature over night. The mixture was extracted with chloroform and the obtained organic layer was washed with water and dried over anhydrous magnesium sulfate. The organic layer was filtrated and the filtrate obtained was concentrated to obtain 1.36 g of the salt of the above-mentioned formula (b), which is called as B1. Yield: 81.6%

$^1$H-NMR (dimethylsulfoxide-d$_6$, Internal standard: tetramethylsilane): δ (ppm) 1.95-1.98 (m, 2H), 2.04-2.06 (m, 2H), 2.15-2.24 (m, 7H), 2.56 (s, 2H), 4.77 (t, 2H, J=15.3 Hz), 7.70-7.80 (m, 15H)

$^{13}$C-NMR (dimethylsulfoxide-d$_6$): δ (ppm) 26.9, 37.3, 38.0, 39.7, 40.2, 45.5, 61.9, 118.8 (t, J=279 Hz), 124.1, 130.9, 131.4, 134.5, 174.5, 216.3

$^{19}$F-NMR (dimethylsulfoxide-d$_6$, Internal standard: fluorobenzene): δ (ppm) 110.7

MS (ESI(+) Spectrum): M$^+$ 263.2 (C$_{18}$H$_{15}$S$^+$=263.09)

MS (ESI(−) Spectrum): M$^−$ 337.0 (C$_{13}$H$_{15}$F$_2$O$_6$S$^−$= 337.06)

Salt Synthesis Example 2

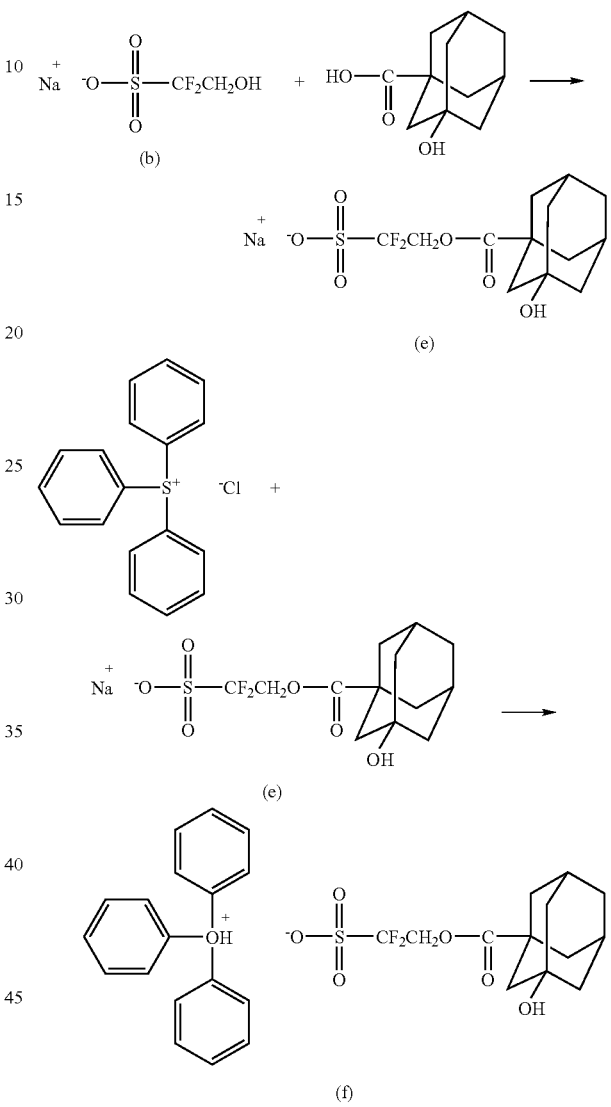

(1) Three point five one grams of 3-hydroxyadamantane-1-carboxylic acid was dissolved in 75 mL of anhydrous tetrahydrofuran. To the obtained solution, a solution prepared by mixing 2.89 g of 1,1'-carbonyldiimidazole with 50 mL of anhydrous tetrahydrofuran was added dropwise at room temperature. The resultant mixture was stirred at room temperature for 4 hours. The mixture was added dropwise to a mixture of 6.04 g of the salt of the above-mentioned formula (b) obtained in the above-mentioned Salt Synthesis Example 1 (1) and 50 mL of anhydrous tetrahydrofuran at 54 to 60° C. over 25 minutes. The resultant mixture was refluxed for 18 hours. After cooling, the reaction mixture was filtrated to remove insoluble matters and insoluble matters were washed with chloroform. The obtained filtrate was concentrated to obtain 6.72 g of the residue. The residue was purified with silica gel chromatography (chloroform/methanol) to obtain 2.99 g of the salt of the above-mentioned formula (e) (yield: 35.8%).

(2) One gram of the salt of the above-mentioned formula (e) obtained in the above-mentioned (1) was dissolved in 30 g of chloroform. To the solution, 6.3 g of aqueous triphenylsulfonium chloride solution (concentration: 13.1%) was added at room temperature. The resultant mixture was stirred at room temperature over night. The mixture was extracted with chloroform and the obtained organic layer was washed with water and dried over anhydrous magnesium sulfate. The organic layer was filtrated and the filtrate obtained was concentrated to obtain 1.6 g of the salt of the above-mentioned formula (f), which is called as B2. Yield: 96.2%

$^1$H-NMR (dimethylsulfoxide-d$_6$, Internal standard: tetramethylsilane): δ (ppm) 1.54 (s, 2H), 1.63-1.70 (m, 4H), 1.73-1.80 (m, 4H), 1.83 (s, 2H), 2.18-2.19 (m, 2H), 2.35 (s, 1H), 4.73 (t, 2H, J=15.3 Hz), 7.68-7.78 (m, 15H)

$^{13}$C-NMR (dimethylsulfoxide-d$_6$): δ (ppm) 30.0, 34.8, 37.4, 44.0, 45.9, 61.7, 119.0 (t, J=279 Hz), 124.3, 131.0, 131.5, 134.5, 175.3

$^{19}$F-NMR (dimethylsulfoxide-d$_6$, Internal standard: fluorobenzene): δ (ppm) 110.6

Salt Synthesis Example 3

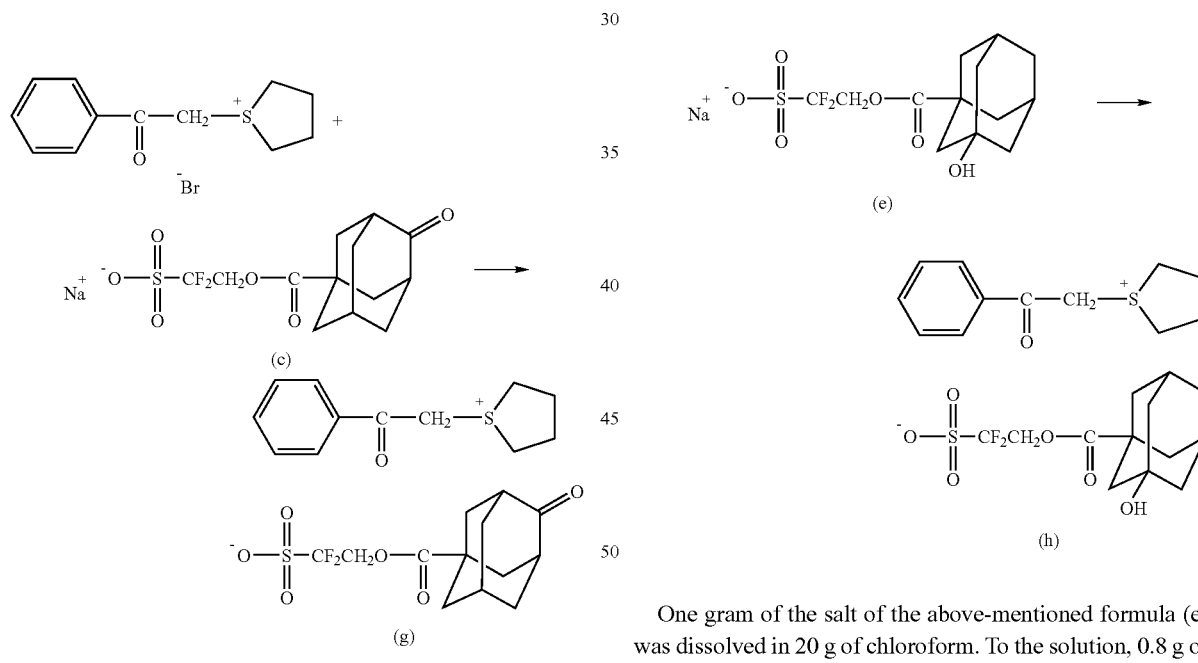

(g)

One gram of the salt of the above-mentioned formula (c) obtained in the above-mentioned Salt Synthesis Example 1 (2) was dissolved in 20 g of chloroform. To the solution, 0.8 g of phenacyltetrahydrothiophenium bromide was added at room temperature. The resultant mixture was stirred at room temperature over night. The mixture was extracted with chloroform and the obtained organic layer was washed with water and dried over anhydrous magnesium sulfate. The organic layer was filtrated and the filtrate obtained was concentrated to obtain 0.9 g of the salt of the above-mentioned formula (g), which is called as B3. Yield: 59.3%

$^1$H-NMR (dimethylsulfoxide-d$_6$, Internal standard: tetramethylsilane): δ (ppm) 1.93-1.96 (m, 2H), 2.01-2.03 (m, 2H), 2.07-2.08 (m, 2H), 2.13 (m, 4H), 2.14 (m, 1H), 2.28-2.33 (m, 4H), 2.46-2.52 (m, 4H), 2.54 (s, 2H), 3.66-3.79 (m, 4H), 4.58 (t, 2H, J=15.3 Hz), 5.56 (s, 2H), 7.47 (m, 2H), 7.61 (m, 1H), 8.01 (d, 2H, J=6.8 Hz)

$^{13}$C-NMR (dimethylsulfoxide-d$_6$): δ (ppm) 27.0, 28.5, 37.3, 38.1, 39.8, 40.3, 45.6, 52.8, 61.2, 118.7 (t, J=278 Hz), 129.0, 129.0, 133.5, 135.0, 174.5, 191.3, 216.4

$^{19}$F-NMR (dimethylsulfoxide-d$_6$, Internal standard: fluorobenzene): δ (ppm) 110.3

MS (ESI(+) Spectrum): M$^+$ 207.1 (C$_{12}$H$_{15}$OS$^+$=207.08)

MS (ESI(−) Spectrum): M$^-$ 337.0 (C$_{13}$H$_{15}$F$_2$O$_6$S$^-$=337.06)

Salt Synthesis Example 4

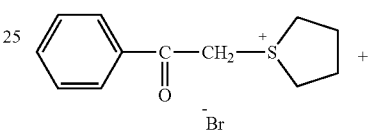

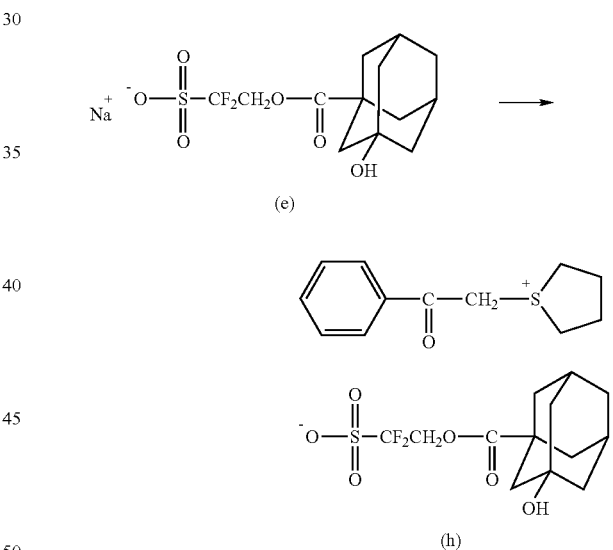

(h)

One gram of the salt of the above-mentioned formula (e) was dissolved in 20 g of chloroform. To the solution, 0.8 g of phenacyltetrahydrothiophenium bromide was added at room temperature. The resultant mixture was stirred at room temperature over night. The mixture was extracted with chloroform and the obtained organic layer was washed with water and dried over anhydrous magnesium sulfate. The organic layer was filtrated and the filtrate obtained was concentrated to obtain 0.6 g of the salt of the above-mentioned formula (h), which is called as B4. Yield: 40.0%

$^1$H-NMR (dimethylsulfoxide-d$_6$, Internal standard: tetramethylsilane): δ (ppm) 1.65 (m, 4H), 1.72 (m, 4H), 1.80 (s, 2H), 2.04 (m, 2H), 2.19 (s, 1H), 2.29-2.37 (m, 4H), 2.48-2.58

(m, 4H), 3.81-3.86 (m, 4H), 4.57 (t, 2H, J=14.9 Hz), 5.89 (s, 2H), 7.47 (m, 2H), 7.61 (m, 1H), 8.01 (d, 2H, J=6.8 Hz)

2H), 2.04-2.06 (m, 2H), 2.15-2.24 (m, 7H), 2.58 (s, 2H), 4.79 (t, 2H, J=15.3 Hz), 7.70 (m, 15H)

Salt Synthesis Example 5

Salt Synthesis Example 6

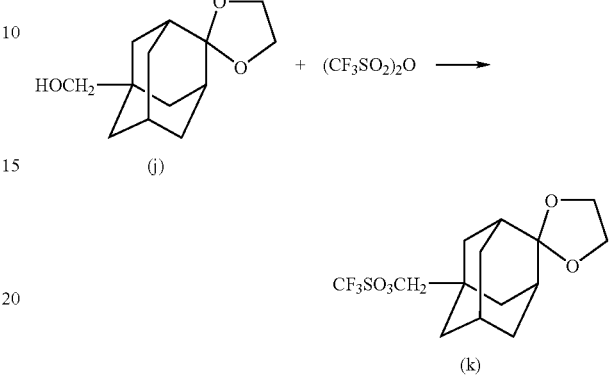

(j)

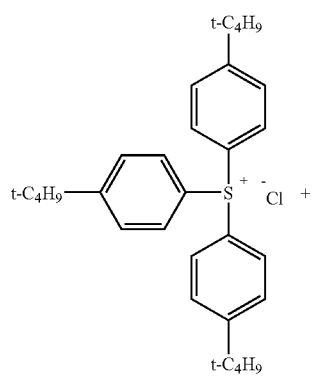

(k)

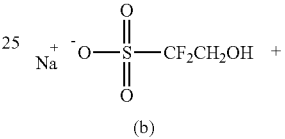

(b)

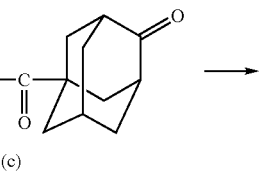

(c)

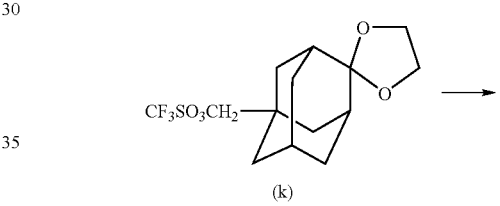

(k)

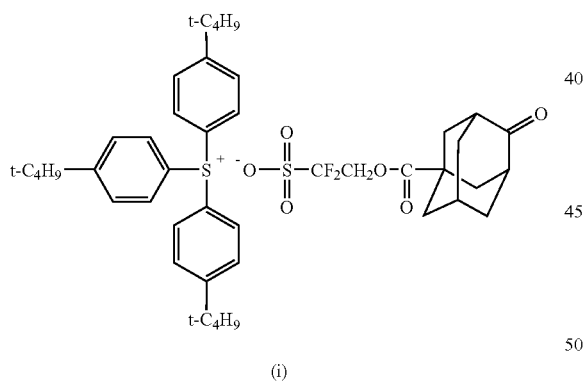

(l)

(i)

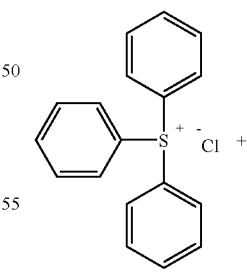

Zero point five gram of the salt of the above-mentioned formula (c) was dissolved in a mixture of 20 g of chloroform and 10 g of water. To the solution, 0.65 g of tris(4-tert-butylphenyl)sulfonium chloride was added at room temperature. The resultant mixture was stirred at room temperature over night. The mixture was extracted with chloroform and the obtained organic layer was washed with water and dried over anhydrous magnesium sulfate. The organic layer was filtrated and the filtrate obtained was concentrated to obtain 0.91 g of the salt of the above-mentioned formula (i), which is called as B5. Yield: 85.0% $^1$H-NMR (CDCl$_3$, Internal standard: tetramethylsilane): δ (ppm) 1.33 (s, 27H), 1.95-1.98 (m,

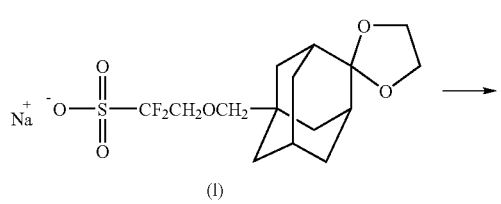

(l)

-continued

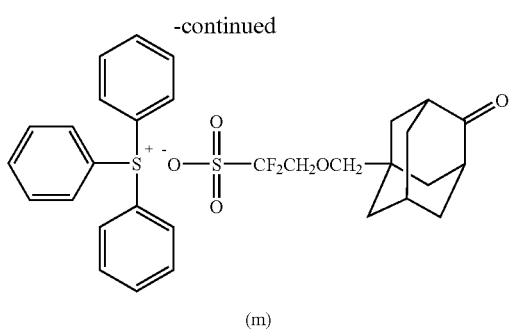

(m)

(1) One gram of the compound of the above-mentioned formula (j) and 2.47 g of pyridine were dissolved in 5 mL of anhydrous dichloromethane. To the resultant solution, the dichloromethane solution prepared by mixing 2.37 g of trifluoromethanesulfonic anhydride and 5 mL of dichloromethane was added dropwise at 3 to 5° C. The resultant mixture was stirred at 3 to 5° C. for 2 hours. Dichloromethane was added to the obtained mixture and the resultant solution was washed with an acidic water, an aqueous sodium hydrogen carbonate solution and water. The solution was dried over anhydrous magnesium sulfate. The mixture was filtrated and the filtrate obtained was concentrated to obtain the residue. The obtained residue was purified with silica gel chromatography (hexane/ethyl acetate) to obtain 1.19 g of the compound of the above-mentioned formula (k). Yield: 74.8%.

$^1$H-NMR (CDCl$_3$, Internal standard: tetramethylsilane): δ (ppm) 1.48-2.07 (m, 13H), 3.95 (s, 4H), 4.10 (s, 2H)

(2) Three milliliter of anhydrous dimethyl sulfoxide and 228.5 mg of sodium hydride were mixed and the resultant mixture was heated to 60° C. To the mixture, 0.62 g of the salt of the above-mentioned formula (b) was added and the resultant mixture was kept at 60° C. for 1 hour. To the mixture, the solution prepared by mixing 1 g of the compound of the above-mentioned formula (k) and 9 mL of anhydrous dimethyl sulfoxide was added dropwise and the resultant mixture was stirred at 60° C. for 5 hours. After the reaction mixture was cooled, the reaction mixture was purified with silica gel chromatography (chloroform/methanol) to obtain 0.28 g of the salt of the above-mentioned formula (l). Yield: 25.6%.

$^1$H-NMR (CDCl$_3$, Internal standard: tetramethylsilane): δ (ppm) 1.69-1.96 (m, 11H), 2.39 (s, 2H), 3.22 (s, 2H), 3.95 (t, 2H, J=15.3 Hz)

(3) Ten gram of chloroform was mixed with 0.2 g of the salt of the above-mentioned formula (l). To the obtained solution, 1.5 g of aqueous triphenylsulfonium chloride solution (concentration: 12.8%) was added at room temperature. The resultant mixture was stirred at room temperature for three days. The mixture was extracted with chloroform and the obtained organic layer was washed with water and dried over anhydrous magnesium sulfate. The organic layer was filtrated and the filtrate obtained was concentrated to obtain 0.24 g of the salt of the above-mentioned formula (m), which is called as B6. Yield: 80.0%

$^1$H-NMR (CDCl$_3$, Internal standard: tetramethylsilane): δ (ppm) 1.70-2.07 (m, 11H), 2.43 (s, 2H), 3.21 (s, 2H), 4.06 (t, 2H, J=15.8 Hz), 7.64-7.74 (m, 15H)

Resin Synthesis Example 1

2-Ethyl-2-adamantyl methacrylate, 3-hydroxy-1-adamantyl methacrylate, 5-methacryloyloxy-2,6-norbornanecarbolactone and α-methacryloyloxy-γ-butyrolactone (monomer molar ratio=2:0.5:0.5:1) are dissolved in 1,4-dioxane. To the solution, 2,2'-azobisisobutyronitrile is added as an initiator, and the resultant mixture is heated at about 85° C. for about 5 hours. The reaction solution is poured into large amount of heptane to cause precipitation. The precipitate is isolated and washed twice with large amount of heptane for purification. As a result, copolymer having a weight-average molecular weight of about 10,000 and degree of dispersion of about 1.7 is obtained. This copolymer is called as resin R1.

Examples 1 to 2 and Comparative Example 1

<Resin>

Resin R1

<Acid Generator>

Acid Generator B1:

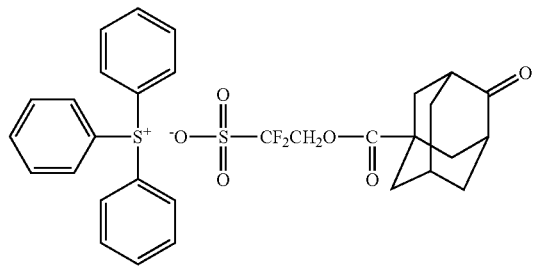

Acid Generator B2:

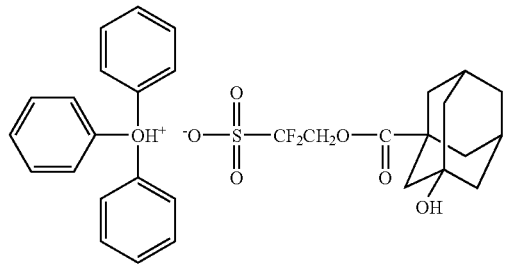

Acid Generator C1:

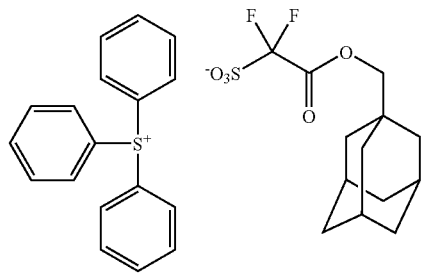

<Quencher>

Quencher Q1: 2,6-diisopropylaniline

<Solvent>

| Solvent Y1: | propylene glycol monomethyl ether acetate | 51.5 parts |
| | 2-heptanone | 35.0 parts |
| | γ-butyrolactone | 3.5 parts |

The following components were mixed to give a solution, and the solution was further filtrated through a fluorine resin filter having a pore diameter of 0.2 μm, to prepare resist liquid.

Resin (kind and amount are described in Table 1)
Acid generator (kind and amount are described in Table 1)
Quencher (kind and amount are described in Table 1)
Solvent (kind and amount are described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 1 | R1/10 | B1/0.27 | Q1/0.0325 | Y1 |
| Ex. 2 | R1/10 | B2/0.27 | Q1/0.0325 | Y1 |
| Comp. Ex. 1 | R1/10 | C1/0.26 | Q1/0.0325 | Y1 |

Silicon wafers were each coated with "ARC-29A-8", which is an organic anti-reflective coating composition available from Nissan Chemical Industries, Ltd., and then baked under the conditions of 205° C. and 60 seconds, to form a 780 Å-thick organic anti-reflective coating. Each of the resist liquids prepared as above was spin-coated over the anti-reflective coating so that the thickness of the resulting film became 0.15 μm after drying. After application of each of the resist liquids, the silicon wafers thus coated with the respective resist liquids were each prebaked on a direct hotplate at a temperature of 125° C. for 60 seconds. Using an ArF excimer stepper ("FPA-5000AS3" manufactured by CANON INC., NA=0.75, 2/3 Annular), each wafer on which the respective resist film had been thus formed was exposed to a line and space pattern, while changing stepwise the exposure quantity.

After the exposure, each wafer was subjected to post-exposure baking on a hotplate at a temperature of 125° C. for 60 seconds and then to paddle development for 15 seconds with an aqueous solution of 2.38% tetramethylammonium hydroxide.

Each of a dark field pattern developed on the organic anti-reflective coating substrate after the development was observed with a scanning electron microscope and line widths were measured to calculate Line Width Roughness (LWR). The results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Effective Sensitivity (ES): It is expressed as the amount of exposure that the line pattern (light-shielding layer) and the space pattern (light-transmitting portion) become 1:1 after exposure through 100 nm line and space pattern mask and development.

Resolution: It is expressed as the minimum size of space pattern which gave the space pattern split by the line pattern at the exposure amount of the effective sensitivity.

LWR: The smaller the value of LWR is, the better the profile of its resist pattern is.

TABLE 2

| Ex. No. | LWR (nm) |
|---|---|
| Ex. 1 | 9.3 |
| Ex. 2 | 8.9 |
| Comp. Ex. 1 | 10.1 |

Apparent from the results shown in Table 2, resist pattern obtained by Examples 1 to 2 have excellent pattern shape because LWR of Examples 1 to 2 are smaller than that of Comparative Example 1.

Example 3

The dark field pattern developed on the organic anti-reflective coating substrate after the development is observed according to a same manner as that of Example 1 except that Acid generator B3 is used in place of Acid generator B1.

Example 4

The dark field pattern developed on the organic anti-reflective coating substrate after the development is observed according to a same manner as that of Example 1 except that Acid generator B4 is used in place of Acid generator B1.

Example 5

The dark field pattern developed on the organic anti-reflective coating substrate after the development is observed according to a same manner as that of Example 1 except that Acid generator B5 is used in place of Acid generator B1.

Example 6

The dark field pattern developed on the organic anti-reflective coating substrate after the development is observed according to a same manner as that of Example 1 except that Acid generator B6 is used in place of Acid generator B1.

The salt represented by the formula (I) is suitably used for an acid generator capable of providing chemically amplified positive resist compositions giving patterns having excellent pattern shape.

What is claimed is:

1. A salt represented by the formula (I):

wherein $Q^1$ and $Q^2$ each independently represent a fluorine atom or a C1-C6 perfluoroalkyl group, T represents a methylene group or a carbonyl group, R represents an adamantyl group substituted with at least one selected from the group consisting of a C1-C4 alkyl group, a C1-C4 alkoxy group, a hydroxyl group, a hydroxymethyl group, a cyano group and an oxo group, and A⁺ represents an organic counter ion.

2. The salt according to claim 1, wherein $Q^1$ and $Q^2$ each independently represent a fluorine atom or a trifluoromethyl group.

3. The salt according to claim 1, wherein $Q^1$ and $Q^2$ represent fluorine atoms.

4. The salt according to claim 1, wherein the organic counter ion is at least one cation selected from the group consisting of a cation represented by the formula (IIa):

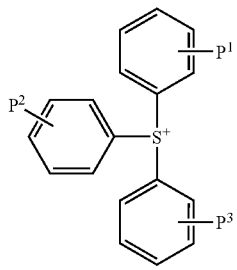

(IIa)

wherein $P^1$, $P^2$ and $P^3$ each independently represent a hydrogen atom, a hydroxyl group, a C1-C12 alkyl group or a C1-C12 alkoxy group, a cation represented by the formula (IIb):

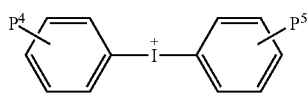

(IIb)

wherein $P^4$ and $P^5$ each independently represent a hydrogen atom, a hydroxyl group, a C1-C12 alkyl group or a C1-C12 alkoxy group, a cation represented by the formula (IIc):

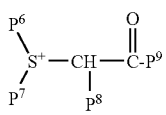

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent S⁺, and at least one —CH₂— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —CH₂— in the divalent acyclic hydrocarbon group may be substituted with —CO—, —O— or —S—, and a cation represented by the formula (IId):

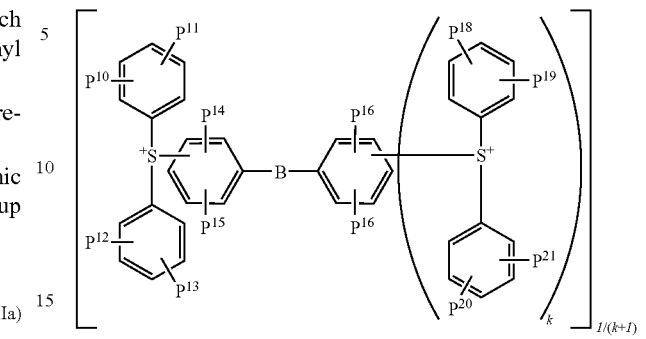

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

5. The salt according to claim 1, wherein the organic counter ion is a cation represented by the formula (IIa).

6. The salt according to claim 5, wherein the cation represented by the formula (IIa) is a cation represented by the formula (IIe):

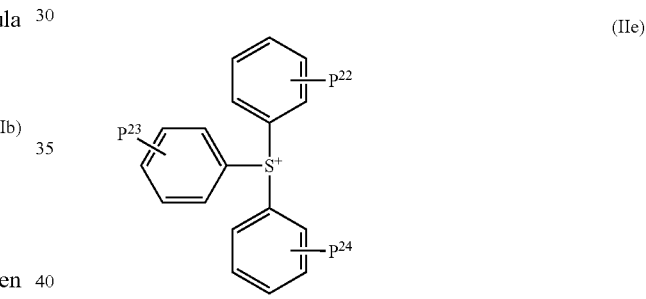

(IIe)

wherein $P^{22}$, $P^{23}$ and $P^{24}$ each independently represent a hydrogen atom or C1-C4 alkyl group.

7. The salt according to claim 1, wherein R represents an adamantyl group substituted with a hydroxyl group or an oxo group.

8. The salt according to claim 7, wherein the organic counter ion is a cation represented by the formula (IIe):

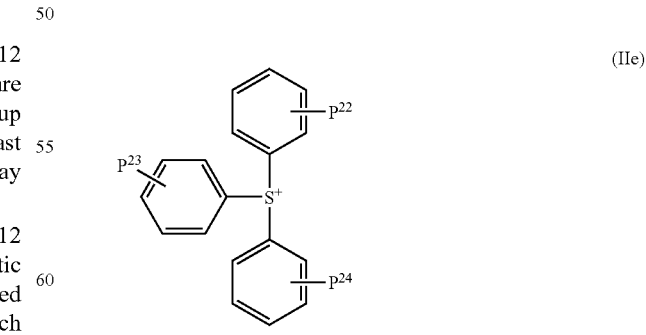

(IIe)

wherein $P^{22}$, $P^{23}$ and $P^{24}$ each independently represent a hydrogen atom or C1-C4 alkyl group.

9. A chemically amplified positive resist composition comprising a salt represented by the formula (I):

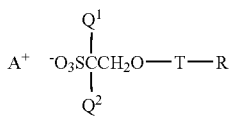

(I)

wherein $Q^1$ and $Q^2$ each independently represent a fluorine atom or a C1-C6 perfluoroalkyl group, T represents a methylene group or a carbonyl group, R represents an adamantyl group substituted with at least one selected from the group consisting of a C1-C4 alkyl group, a C1-C4 alkoxy group, a hydroxyl group, a hydroxymethyl group, a cyano group and an oxo group, and $A^+$ represents an organic counter ion, and a resin which contains a structural unit which has an acid-labile group and which itself is insoluble or poorly soluble in an aqueous alkali solution but becomes soluble in an aqueous alkali solution by the action of an acid.

10. The chemically amplified positive resist composition according to claim 9, wherein $Q^1$ and $Q^2$ each independently represent a fluorine atom or a trifluoromethyl group.

11. The chemically amplified positive resist composition according to claim 9, wherein $Q^1$ and $Q^2$ represent fluorine atoms.

12. The chemically amplified positive resist composition according to claim 9, wherein the resin contains a structural unit derived from a monomer having a bulky and acid-labile group.

13. The chemically amplified positive resist composition according to claim 12, wherein the bulky and acid-labile group is a 2-alkyl-2-adamantyl ester group or a 1-(1-adamantyl)-1-alkylalkyl ester group.

14. The chemically amplified positive resist composition according to claim 12, wherein the monomer having a bulky and acid-labile group is 2-alkyl-2-adamantyl acrylate, 2-alkyl-2-adamantylmethacrylate, 1-(1-adamantyl)-1-alkylalkyl acrylate, 1-(1-adamantyl)-1-alkylalkyl methacrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate.

15. The chemically amplified positive resist composition according to claim 12, wherein the monomer having a bulky and acid-labile group is 2-alkyl-2-adamantylacrylate, 2-alkyl-2-adamantyl methacrylate, 1-(1-adamantyl)-1-alkylalkylacrylate and 1-(1-adamantyl)-1-alkylalkyl methacrylate.

16. The chemically amplified positive resist composition according to claim 12, wherein the monomer having a bulky and acid-labile group is 2-alkyl-2-adamantyl acrylate and 2-alkyl-2-adamantyl methacrylate.

17. The chemically amplified positive resist composition according to claim 9, wherein the chemically amplified positive resist composition further comprises a basic compound.

* * * * *